US010363072B2

(12) United States Patent
Bauerle et al.

(10) Patent No.: US 10,363,072 B2
(45) Date of Patent: Jul. 30, 2019

(54) VERTEBRAL PLATE REVISION APPARATUSES, KITS, AND METHODS AND OSTEOSYNTHESIS SYSTEMS

(71) Applicant: DeGen Medical, Inc., Florence, SC (US)

(72) Inventors: Wayne B. Bauerle, Myrtle Beach, SC (US); Kidong Yu, Florence, SC (US); Craig Black, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 668 days.

(21) Appl. No.: 15/046,727

(22) Filed: Feb. 18, 2016

(65) Prior Publication Data
US 2016/0235449 A1 Aug. 18, 2016

Related U.S. Application Data

(60) Provisional application No. 62/117,765, filed on Feb. 18, 2015.

(51) Int. Cl.
*A61B 17/80* (2006.01)
*A61B 17/70* (2006.01)

(52) U.S. Cl.
CPC ...... *A61B 17/7059* (2013.01); *A61B 17/8004* (2013.01); *A61B 17/8023* (2013.01); *A61B 17/8042* (2013.01)

(58) Field of Classification Search
CPC ............ A61B 17/7014; A61B 17/7044; A61B 17/7059; A61B 17/8004; A61B 17/8023; A61B 17/8042
See application file for complete search history.

(56) References Cited

U.S. PATENT DOCUMENTS

| | | |
|---|---|---|
| 4,503,848 A | 3/1985 | Caspar et al. |
| 6,152,927 A | 11/2000 | Farris et al. |
| 6,645,208 B2 | 11/2003 | Apfelbaum et al. |
| D505,205 S | 5/2005 | Freid |
| 7,097,645 B2 | 8/2006 | Michelson |
| 7,166,111 B2 | 1/2007 | Kolb et al. |
| 7,303,564 B2 | 12/2007 | Freid et al. |
| 7,326,212 B2 | 2/2008 | Huebner |
| 7,547,306 B2 | 6/2009 | Michelson |
| 7,572,282 B2 | 8/2009 | Boomer et al. |
| 7,985,224 B2 | 7/2011 | Michelson |
| 8,070,749 B2 | 12/2011 | Stern |
| 8,128,628 B2 | 3/2012 | Freid et al. |
| 8,556,895 B2 | 10/2013 | Stern |
| 8,636,738 B2 | 1/2014 | McClintock et al. |
| 8,652,179 B2 | 2/2014 | Graham et al. |

(Continued)

FOREIGN PATENT DOCUMENTS

WO    WO03013623    2/2003

*Primary Examiner* — Anu Ramana
(74) *Attorney, Agent, or Firm* — Buchanan Van Tuinen LLC

(57) ABSTRACT

Vertebral plate revision apparatuses, kits, and methods, and osteosynthesis systems useful in the treatment of vertebrae are described. An example vertebral plate revision apparatus is comprised of an extension plate, a connecting plate, a connecting member, and a set of locking members. An example osteosynthesis system comprises a vertebral plate revision apparatus, a previously-implanted plate, and a set of anchors.

20 Claims, 16 Drawing Sheets

(56) References Cited

U.S. PATENT DOCUMENTS

| | | |
|---|---|---|
| 8,858,556 B2 | 10/2014 | Stern |
| 9,119,682 B2 * | 9/2015 | Stoll .................. A61B 17/8028 |
| 2005/0107795 A1 | 5/2005 | Morris et al. |
| 2006/0009845 A1 | 1/2006 | Chin |
| 2006/0116681 A1 | 6/2006 | Bert |
| 2006/0122607 A1 | 6/2006 | Kolb |
| 2006/0235409 A1 | 10/2006 | Blain |
| 2007/0233108 A1 | 10/2007 | Stalcup et al. |
| 2009/0163960 A1 | 6/2009 | Binder et al. |

* cited by examiner

VERTEBRAL PLATE REVISION APPARATUSES, KITS, AND METHODS AND OSTEOSYNTHESIS SYSTEMS

FIELD

The disclosure relates to the technical field of vertebral plate revision apparatuses, kits, and methods and osteosynthesis systems useful for connecting bones or portions of bones to each other in an animal, such as a human.

BACKGROUND

The art includes several examples of apparatuses, systems, kits, and methods useful for connecting bones or portions of bones to each other through the use of interconnected vertebral plates. Several designs, for example, include previously-implanted plates that span the bones or portions of bones to be connected, anchors that secure the previously-implanted plates to the bones or portions of bones, and a revision plate connected to the previously-implanted plate and the bones or portions of bones. In one example, described in U.S. Pat. No. 8,858,556, the revision plate is connected to a previously-implanted plate via horizontal movement of the revision plate relative to the previously-implanted plate.

Despite this and other examples, a need exists for improved vertebral plate revision apparatuses, kits, and methods and osteosynthesis systems.

BRIEF SUMMARY OF EXAMPLES

Various example vertebral plate revision apparatuses useful for connecting bones or portions of bones to each other in an animal such as a human are described and illustrated herein.

An example vertebral plate revision apparatus comprises an extension plate having an upper surface, a lower surface, a side extending from the upper surface to the lower surface, a set of anchor passageways extending from the upper surface to the lower surface, a set of locking member passageways extending from the upper surface to the lower surface, and a connecting member recess having an upper surface and a lower surface, the connecting member recess defining a connecting member passageway extending from the upper surface to the lower surface of the connecting member recess; a connecting plate having an upper surface, a lower surface, a side extending from the upper surface to the lower surface, a set of anchor passageways extending from the upper surface to the lower surface, a set of locking member passageways extending from the upper surface to the lower surface, a connecting member recess, a connecting member bossboss disposed on the connecting member recess, and an engaging recess, the connecting member bossboss disposed within the connecting member passageway of the extension plate; and a connecting member having an upper surface, a lower surface, a side extending from the upper surface to the lower surface, and a channel extending from the upper surface to the lower surface, the connecting member releasably attached to the connecting member bossboss of the connecting plate and in contact with the connecting member recess of the extension plate; wherein the set of anchor passageways of the extension plate are substantially aligned with the set of anchor passageways of the connector plate.

Furthermore, various example methods of engaging a vertebral plate revision apparatus with a previously-implanted plate are described and illustrated herein.

An example method of engaging a vertebral plate revision apparatus having a connecting plate and an extension plate, such as a vertebral plate revision apparatus according to an example described herein, with a previously-implanted plate having an anchor disposed through an anchor passageway comprises the steps of removing the anchor from the previously-implanted plate; placing the connecting plate over the previously-implanted plate such that an anchor passageway of the connecting plate is aligned with the anchor passageway of the previously-implanted plate; stabilizing the connecting plate relative to the extension plate; and inserting the anchor through the aligned anchor passageways of the connecting plate and the previously-implanted plate such that the connecting plate is secured to the previously-implanted plate.

Additional understanding of the vertebral plate revision apparatuses and methods of engaging a vertebral plate revision apparatus with a previously-implanted plate can be obtained with review of the detailed description, below, and the appended drawings.

DESCRIPTION OF EMBODIMENTS

Figure 1:
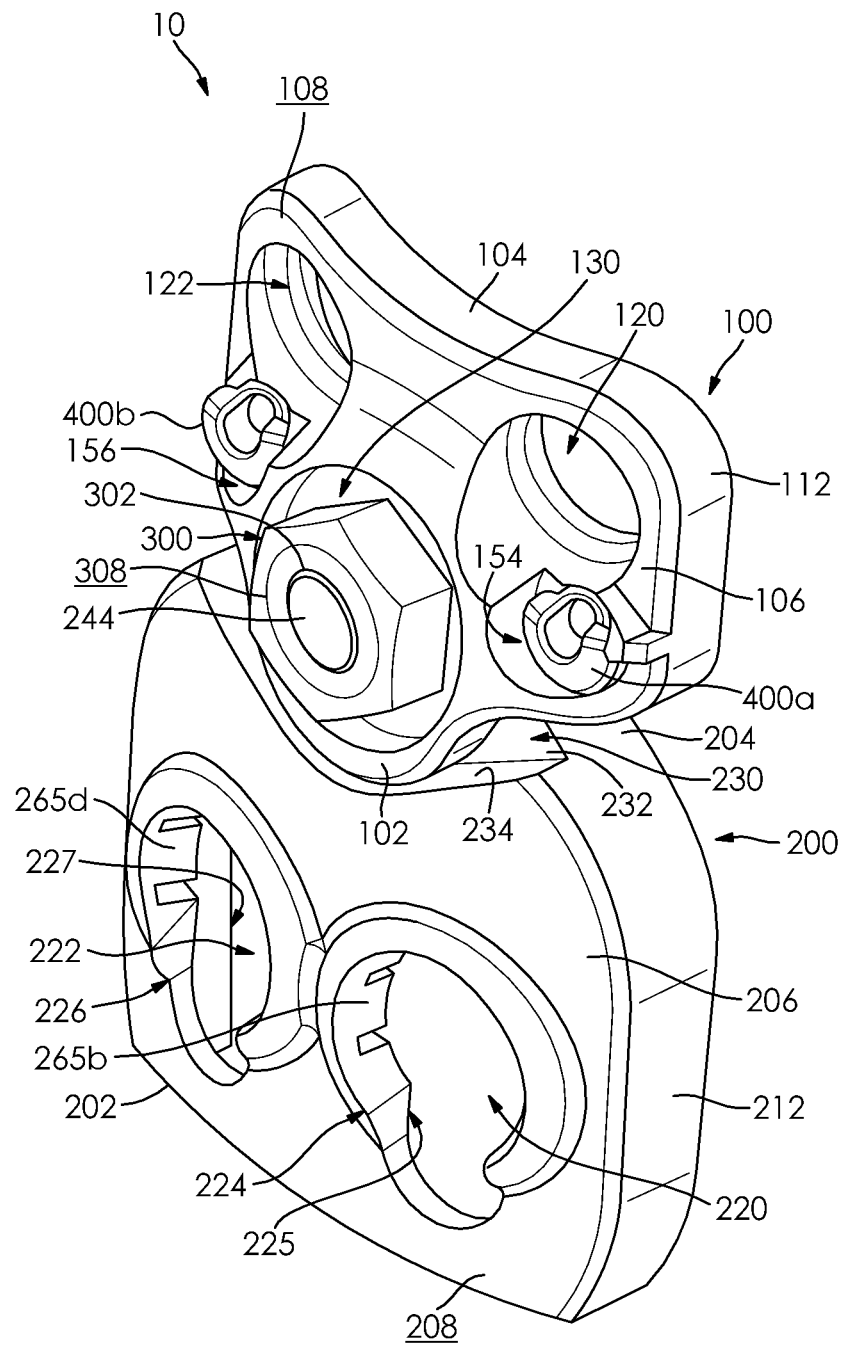
FIG. 1 is a perspective view of a vertebral plate revision apparatus.

The following detailed description and the appended drawings describe and illustrate various example embodiments. The description and illustration of these examples are provided to enable one skilled in the art to make and use vertebral plate revision apparatuses, kits, and methods and osteosynthesis systems. They are not intended to limit the scope of the claims in any manner.

As used herein, the term "engage" and grammatically related terms means to make contact with a structure.

In the drawings and the description, a reference number followed by a lower case letter, e.g., 400a, refers to a specific structure that is a member of a group of related structures that are denoted by the same reference number but with a different letter, e.g., 400b. For example, in FIG. 1, the specific locking members are indicated by reference numbers 400a and 400b.

Each of FIGS. 1, 2, 3, 4, 5, and 6 illustrates a first example vertebral plate revision apparatus 10. The vertebral plate revision apparatus 10 includes an extension plate 100, a connecting plate 200, a connecting member 300, and a set of locking members 400a, 400b.

The extension plate 100 comprises a proximal end 102, a distal end 104, a main body 106 extending from the proximal end 102 to the distal end 104, an upper surface 108, a lower surface 110, and a side 112 extending from the upper surface 108 to the lower surface 110. The extension plate defines a set of anchor passageways 120, 122, a connecting member recess 130, a connecting member passageway 140, and a set of locking member passageways 150, 152, as well.

Figure 6:
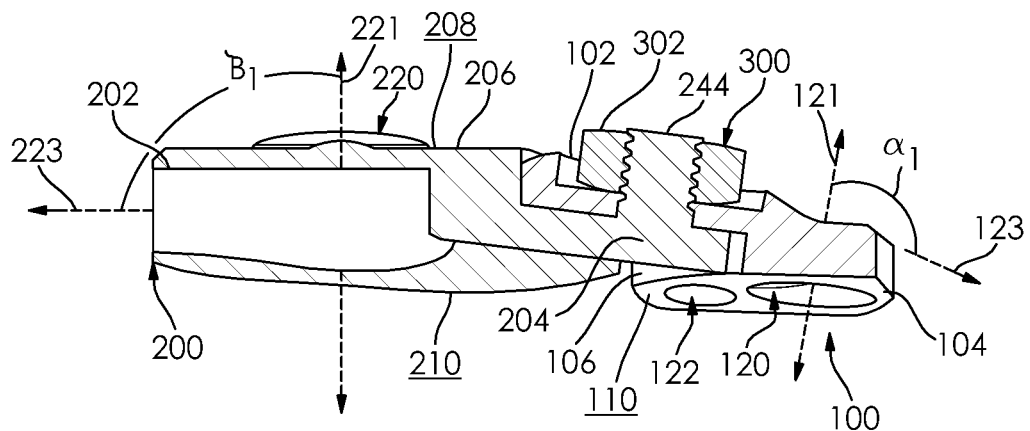
FIG. 6 is a sectional view of the vertebral plate revision apparatus illustrated in FIG. 1, taken along line 6-6 in FIG. 5.

In the illustrated embodiment, each of the anchor passageways 120, 122 extends from the upper surface 108 to the lower surface 110 of the main body 106 and is disposed distal to the connecting member recess 130. Each of the anchor passageways 120, 122 has a central axis that lies on a plane that is disposed at an angle to a plane that contains a central longitudinal axis of the extension plate 100. For example, as best illustrated in FIG. 6 the first anchor passageway 120 has a central axis that lies on a first plane 121, which is disposed at a first angle $\alpha_1$ to a second plane 123, which contains the central longitudinal axis of the main body 106 of the extension plate 100. Similarly, the second anchor passageway 122 has a central axis that lies on a third plane (not illustrated in the Figures), which is disposed at a second angle (not illustrated in the Figures) to the second plane 123, which contains the central longitudinal axis of the main body 106 of the extension plate 100. This configuration places anchors (described below) disposed within the anchor passageways 120, 122 at an angle to the second plane 123 that contains central longitudinal axis of the main body 106 of the extension plate 100. The anchor passageways 120, 122 can be disposed at any suitable angle, and a skilled artisan will be able to select appropriate angles according to a particular embodiment based on various considerations, including the intended use and location at which the particular vertebral plate revision apparatus will be implanted. In this embodiment, first and second anchor passageways 120, 122 are disposed on one end of the extension plate 100 and are configured such that the first angle $\alpha_1$ is inverse to the second angle (not illustrated in the Figures) relative to the second plane 123. In various embodiments, the first angle can be between about 10° and about 90°, between about 25° and about 75°, and between about 40° and about 60° in various embodiments. The second angle can be between about −10° and about −90°, between about −25° and about −75°, and between about −40° and about −60° in various embodiments, as well. It is noted, though, that different angles and numbers of anchor passageways can be used and, indeed, each of the anchor passageways in a vertebral plate revision apparatus according to a particular embodiment can be disposed at an angle that is different from one, more than one, or all of the anchor passageways defined by the plates of the particular vertebral plate revision apparatus.

The first and second anchor passageways 120, 122 define first and second diameters $d_1$, $d_2$, respectively. In the illustrated embodiment, the first diameter $d_1$ is equal to the second diameter $d_2$. A skilled artisan will be able to determine suitable first and second diameters based on various considerations, including the intended use and location at which the particular vertebral plate revision apparatus will be implanted. In an alternative embodiment, the first diameter may be less than the second diameter. In a different embodiment, the first diameter may be greater than or about equal to the second diameter.

The main body 106 also defines two locking member passageways 150, 152, which respectively define locking member openings 154 and 156. Each locking member passageway 150, 152 extends from the upper surface 108 to the lower surface 110. Each of the locking member passageways 150, 152 has an upper portion (not illustrated in the Figures) and a lower portion (not illustrated in the Figures). The upper portions are in communication with their adjacent anchor passageways 120, 122. Additionally, the lower portions of the locking member passageways 120, 122 are cylindrical in shape. A skilled artisan will be able to determine whether to include a set of locking member passageways, how many locking member passageways to include, and how best to configure the locking member passageways based on various considerations, including the intended use and location at which the particular vertebral plate revision apparatus will be implanted. In an alternative embodiment, the main body may define more than or less than two locking member passageways. In a different embodiment, the entire locking member passageways may be in communication with their respective adjacent locking member passageways. In another embodiment, any portion of the locking member passageways, including the upper portion, lower portion, or both portions, may have any shape, including conical, cylindrical, or spherical.

The first and second locking member passageways 150, 152 define third and fourth diameters $d_3$, $d_4$, respectively. In the illustrated embodiment, the third diameter $d_3$ is equal to the fourth diameter $d_4$. Each of the third and fourth diameters $d_3$, $d_4$ is also less than each of the first and second diameters $d_1$, $d_2$. The third and fourth diameters are, however, great enough to allow for the first and second locking member passageways 150, 152 to engage the locking members 400a, 400b, respectively. A skilled artisan will be able to determine suitable third and fourth diameters based on various considerations, including the intended use and location at which the particular vertebral plate revision apparatus will be implanted. In an alternative embodiment, the third diameter may be less than the fourth diameter. In a different embodiment, the third diameter may be greater than or about equal to the fourth diameter.

The main body 106 of the extension plate 100 also defines a connecting member recess 130, which comprises a base 132 and a side 134, and is disposed proximal to the anchor passageways 120, 122. The connecting member recess 130 extends from the upper surface 108 of the main body 106 toward the lower surface 110; it does not reach the lower surface 110, however. The base 132 of the connecting member recess 130 is substantially circular in shape and defines a connecting member upper passageway opening 142, which is also circular in shape. The connecting member passageway upper opening 142 surrounds the center (not illustrated in the Figures) of the connecting member recess 130. The side 134 is substantially rectangular. A skilled artisan will be able to determine suitable shapes for the base and side of the connecting member recess and for the connecting member passageway upper opening based on various considerations, including the intended use and location at which the particular vertebral plate revision apparatus will be implanted. In an alternative embodiment, the base of the connecting member recess may be triangular, elliptical, rectangular, square, or any other shape. In another embodiment, the side of the connecting member recess may be triangular, elliptical, rectangular, square, or any other shape. In a different embodiment, the connecting member passageway upper opening may be triangular, elliptical, rectangular, square, or any other shape. Furthermore, the connecting member passageway upper opening may be defined by the base at a position other than the position at which the connecting member passageway upper opening surrounds the center of the base. The extension plate may also define no connecting member recess in another embodiment.

The main body 106 defines a connecting member passageway 140, as well. The connecting member passageway 140 extends from the connecting member passageway lower opening 144 defined by lower surface 110 to the connecting member passageway upper opening 142 defined by the base 132. The connecting member passageway 140 is substantially cylindrical in the illustrated embodiment and the connecting member passageway lower opening 144 is substantially circular. A skilled artisan will be able to determine suitable shapes for the connecting member passageway and for the connecting member passageway lower opening based on various considerations, including the intended use and location at which the particular vertebral plate revision apparatus will be implanted. In an alternative embodiment, the connecting member passageway may be conical, spheroid, spherical, pyramidal, or any other shape. In a different embodiment, the connecting member passageway lower opening may be triangular, elliptical, rectangular, square, or any other shape.

The connecting member passageway upper opening 142 and the connecting member passageway lower opening 144 define fifth and sixth diameters $d_5$, $d_6$, respectively. In the illustrated embodiment, the fifth diameter $d_5$ is equal to the sixth diameter $d_6$. Each of the fifth and sixth diameters $d_5$, $d_6$ is also less than each of the third and fourth diameters $d_3$, $d_4$. The fifth and sixth diameters $d_5$, $d_6$ must, however, be great enough to allow for at least a portion of the connecting plate (described below) to engage the connecting member passageway 140. A skilled artisan will be able to determine suitable fifth and sixth diameters based on various considerations, including the intended use and location at which the particular vertebral plate revision apparatus will be implanted. In an alternative embodiment, the fifth diameter may be less than the sixth diameter. In a different embodiment, the fifth diameter may be greater than or about equal to the sixth diameter.

Figure 4:
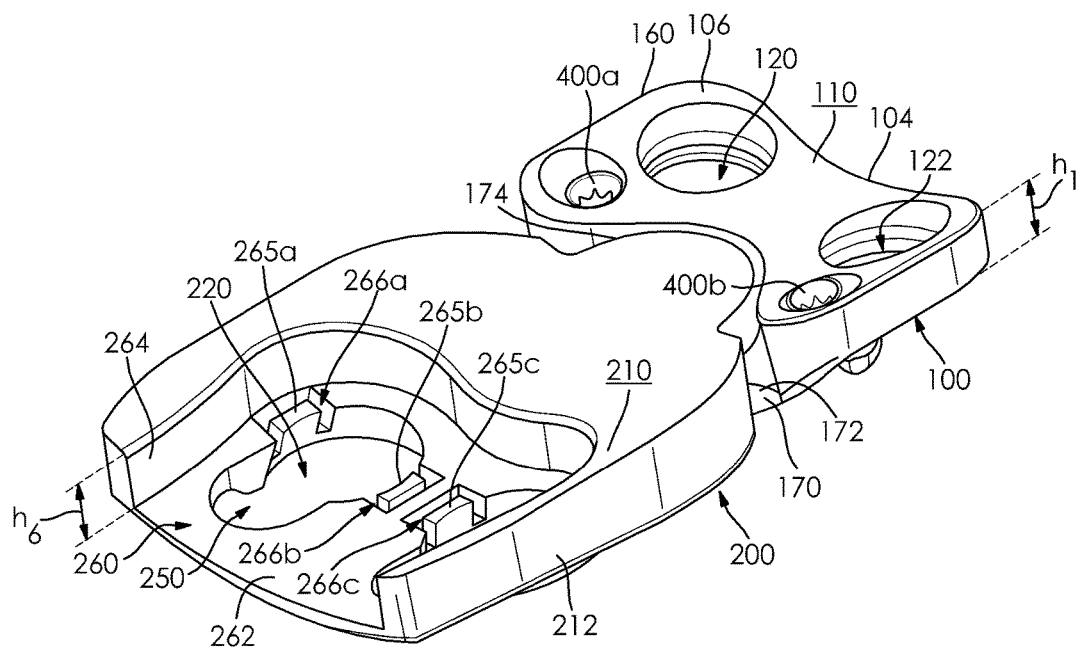
FIG. 4 is another perspective view of the vertebral plate revision apparatus illustrated in FIG. 1.
Figure 5:
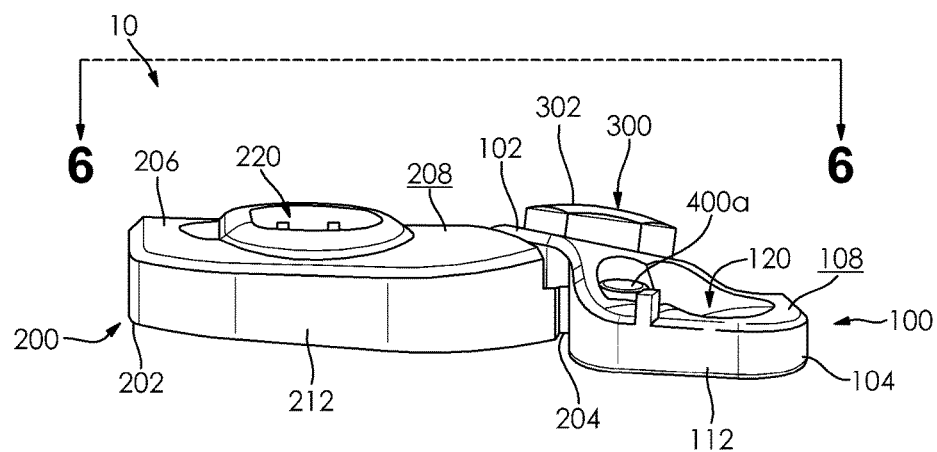
FIG. 5 is a side view of the vertebral plate revision apparatus illustrated in FIG. 1.

As best illustrated in FIG. 4, the main body 106 and the lower surface 110 cooperatively define a first portion 160 and a second portion 170. The first portion 160 defines the locking member passageways 150, 152 and the anchor passageways 120, 122, along with the main body 106 and the upper surface 108, while the second portion 170 defines the connecting member passageway lower opening 144. The side 112 extends around the entire first portion 160 and is adjacent the second portion 170, which includes a base 172 adjacent the side 112 and a second side 174. The base 172 and the second side 174 are elevated in relation to the lower surface 112 and are configured to engage the connecting plate 200 (described below). Additionally, the first portion 160 is configured to engage a bone or a portion of a bone. A skilled artisan will be able to determine how best to configure and shape the first and second portions based on various considerations, including the intended use and location at which the particular vertebral plate revision apparatus will be implanted. In an alternative embodiment, the entire lower surface may be disposed on one plane. In a different embodiment, the entire lower surface may be arcuate in shape. In another embodiment, the second portion may be lowered relative to the first portion or may be elevated to any degree relative to the first portion. Furthermore, in other embodiments, each of the lower portion and upper portion may have any shape, including square, triangular, elliptical, rectangular, or any other shape.

In the illustrated embodiment, the side 112 defines a first height $h_1$ that extends from where the side 112 is adjacent the upper surface 108 and the first portion 160 of the lower surface 110. The side 174 of the second portion 170 defines a second height (not illustrated in the Figures) that extends from where the side 174 is adjacent the upper surface 108 to where the side 174 is adjacent the base 172. In the illustrated embodiment, the first height $h_1$ is greater than the second height. A skilled artisan will be able to determine suitable first and second heights based on various considerations, including the intended use and location at which the particular vertebral plate revision apparatus will be implanted. In an alternative embodiment, the first height may be less than the second height. In a different embodiment, the first height may be greater than or about equal to the second height.

The connecting plate 200 comprises a proximal end 202, a distal end 204, a main body 206 extending from the proximal end 202 to the distal end 204, an upper surface 208, a lower surface 210, and a side 212 extending from the upper surface 208 to the lower surface 210. The connecting plate 200 defines a set of anchor passageways 220, 222, a connecting member recess 230, a connecting member boss 240, such as the threaded post illustrated in the Figures, a set of locking member passageways 250, 252, and an engaging recess 260.

In the illustrated embodiment, each of the anchor passageways 220, 222 extends from the upper surface 208 of the main body 206 to the base (described below) of the engaging recess 260 and is disposed proximal to the engaging recess 260. Each of the anchor passageways 220, 222 also defines respective upper openings 224, 226 and lower openings 225, 227. Each of the anchor passageways 220, 222 has a central axis that lies on a plane that is disposed at an angle to a plane that contains a central longitudinal axis of the connecting plate 200, as well. For example, as best illustrated in FIG. 6 the first anchor passageway 220 has a central axis that lies on a first plane 221, which is disposed at a first angle $\beta_1$ to a second plane 223, which contains the central longitudinal axis of the main body 206 of the connecting plate 200. Similarly, the second anchor passageway (not illustrated in the Figures) has a central axis that lies on a third plane (not illustrated in the Figures), which is disposed at a second angle (not illustrated in the Figures) to the second plane 223, which contains the central longitudinal axis of the main body 206 of the connecting plate 200. This configuration places anchors (described below) disposed within the anchor passageways 220, 222 at an angle to the second plane 223 that contains central longitudinal axis of the main body 206 of the connecting plate 200. The anchor passageways 220, 220 can be disposed at any suitable angle, and a skilled artisan will be able to select appropriate angles according to a particular embodiment based on various considerations, including the intended use and location at which the particular vertebral plate revision apparatus will be implanted. The first and second anchor passageways 220, 222 are disposed on the proximal end 202 of the connecting plate 222, the connecting member recess 230 is disposed at the distal end 204, and the first and second anchor passageways 220, 222 are configured such that the first angle $\beta_1$ is inverse to the second angle (not illustrated in the Figures) relative to the second plane 223. For example, the first angle can be between about 10° and about 90°, between about 25° and about 75°, and between about 40° and about 60° in various embodiments. The second angle can be between about −10° and about −90°, between about −25° and about −75°, and between about −40° and about −60° in various embodiments, as well. It is noted, though, that different angles can be used and, indeed, each of the anchor passageways in a vertebral plate revision apparatus according to a particular embodiment can be disposed at an angle that is different from one, more than one, or all of the anchor passageways defined by the plates of the particular vertebral plate revision apparatus.

The first and second anchor passageways 220, 222 define seventh and eighth diameters $d_7$, $d_8$, respectively. In the illustrated embodiment, the seventh diameter $d_7$ is equal to the eighth diameter $d_8$. A skilled artisan will be able to determine suitable seventh and eighth diameters based on various considerations, including the intended use and location at which the particular vertebral plate revision apparatus will be implanted. In an alternative embodiment, the seventh diameter may be less than the eighth diameter. In a different embodiment, the seventh diameter may be greater than or about equal to the eighth diameter.

The main body 206 also defines locking member passageways 250, 252, which respectively define locking member upper openings 254, 256, and locking member lower openings 255, 257. Each locking member passageway 250, 252 extends from the upper surface 208 to the base of the engaging recess 262 (described below). Each of the locking member passageways 250, 252 is in communication with the adjacent one of the anchor passageways 220, 222. Additionally, the locking member passageways 220, 222 are semi-cylindrical in shape. A skilled artisan will be able to determine whether to include a set of locking member passageways, how many locking member passageways to include, and how best to configure the locking member passageways based on various considerations, including the intended use and location at which the particular vertebral plate revision apparatus will be implanted. In an alternative embodiment, the main body may define more than two locking member passageways. In a different embodiment, the only a portion of the locking member passageways may be in communication with their respective adjacent anchor passageways. In another embodiment, the locking member passageways may have any shape, including conical, cylindrical, or spherical.

The first and second locking member passageways 250, 252 define ninth and tenth diameters $d_9$, $d_{10}$, respectively. In the illustrated embodiment, the ninth diameter $d_9$ is equal to the tenth diameter $d_{10}$. Each of the ninth and tenth diameters $d_9$, $d_{10}$ are also less than each of the seventh and eighth diameters $d_7$, $d_8$. The ninth and tenth diameters are, however, great enough to allow for the first and second locking member passageways 250, 252 to engage a locking member (described below). A skilled artisan will be able to determine suitable ninth and tenth diameters based on a various considerations, including the intended use and location at which the particular vertebral plate revision apparatus will be implanted. In an alternative embodiment, the ninth diameter may be less than the tenth diameter. In a different embodiment, the ninth diameter may be greater than or about equal to the tenth diameter.

The main body 206 of the connecting plate 200 also defines a connecting member recess 230, which in turn defines a base 232, a first side 234, a second side 235, and a connecting member boss 240. The base 232 extends from the lower surface 210 of the main body 206 toward the upper surface 208, but does not reach the upper surface 208. The first side 234 is arcuate in shape and extends from the surface 231 of the base 232 to the upper surface 208 of the main body 206. The second side 235 is substantially bell-shaped and extends from the surface 231 of the base 232 to the lower surface 210 of the main body 206. The base 232 extends from the first side 234 to the second side 235. Additionally, the connecting member boss 240 is disposed on the surface 231 of the base 232. A skilled artisan will be able to determine suitable shapes for the base and sides of the connecting member recess based on various considerations, including the intended use and location at which the particular vertebral plate revision apparatus will be implanted. In an alternative embodiment, the base of the connecting member recess may be triangular, elliptical, rectangular, square, or any other shape. In another embodiment, the first and second sides of the connecting member recess may be triangular, elliptical, rectangular, square, or any other shape. The connecting plate may also define no connecting member recess in another embodiment.

In the illustrated embodiment, the side 212 of the main body 206 defines a third height $h_3$ that extends from where the side 212 is adjacent the upper surface 208 and the lower surface 210. The first side 234 of the connecting member recess 230 defines a fourth height $h_4$ extending from the upper surface 208 to the surface 231 of the base 232. The second side 235 of the connecting member recess 230 defines a fifth height $h_5$ extending from the lower surface 210 to the surface 231 of the base 232. In the illustrated embodiment, the third height $h_3$ is greater than each of the fourth and fifth heights $h_4$, $h_5$. The fourth and fifth heights $h_4$, $h_5$, however, are substantially equal to one another in this embodiment. A skilled artisan will be able to determine suitable third, fourth, and fifth heights based on various considerations, including the intended use and location at which the particular vertebral plate revision apparatus will be implanted. In an alternative embodiment, the third height may be less than the fourth and fifth heights. In a different embodiment, the third height may be greater than or about equal to the fourth height and fifth heights. In other embodiments, the fourth height may be greater than, equal to, about equal to, or less than the fifth height.

The connecting member boss 240 that is disposed on the surface 231 of the base 232 includes a shaft 242, a tip 244, and an outer surface 246. The shaft 242 extends from the surface 231 of the base 232 to the tip 244 and is substantially cylindrical in shape. The tip 244 is substantially circular in shape and is configured to be inserted into the connecting member passageway 140 of the extension plate 100. In the illustrated embodiment, the tip 244 of the connecting member boss 240 extends past the connecting member passageway upper opening 142 when it is inserted into the connecting member passageway 140. In addition, the outer surface 246 includes threads 248 that are configured to mate with threads defined by the connecting member 300 (described below). Thus, the connecting member boss 240 connects the extension plate 100, the connecting plate 200, and the connecting member 300. A skilled artisan will be able to determine suitable shapes for the shaft and tip of the connecting member boss based on various considerations, including the intended use and location at which the particular vertebral plate revision apparatus will be implanted. In a different embodiment, the shaft may be cylindrical, spherical, pyramidal, or any other shape. Alternatively, the connecting member boss may not include threads. In another embodiment, the tip may be square, rectangular, triangular, elliptical, or any other shape. Furthermore, in other embodiments, a rivet, a screw, a rod, any other mechanical attachment mechanism, or an adhesive may be used in place of the connecting member boss to connect the extension plate, connecting late, and connecting member.

In use, the first side 234 and base 232 of the connecting member recess 230 of the connecting plate 200 are in contact with the base 172 and side 174 of the second portion 170 of the extension plate 100. In the illustrated embodiment, prior to the introduction of the connecting member 300, the extension plate 100 may be pivotally adjusted relative to the connecting plate 200 in either direction about the connecting member boss 240 when the side 174 is in contact with the first side 234 of the connecting member recess 230 of the connecting plate 200. This allows for the extension plate 100 to be adjusted to suitably position the vertebral plate revision apparatus 10 relative to the contours of a particular bone or portion of a bone (not illustrated in the Figures). Once a suitable alignment of, particularly, the side 174 of the second portion 170 of the extension plate 100 and the first side 234 of the connecting member recess 230 of the connecting plate 200 has been determined, a connecting member 300 may be used to hold the connecting and extension 200, 100 plates in place. A skilled artisan will be able to determine whether to allow for such pivotal movement and whether to allow for such movement through a different mechanism based on various considerations, including the intended use and location at which the particular vertebral plate revision apparatus will be implanted. In other embodiments, the side of the extension plate may be inserted into a slot defined by the connecting plate and adjusted once it is positioned in the slot. In a different embodiment, the side of the connecting plate may be placed atop the side of the extension plate and attached via a connecting member. Additionally, the sides of the connecting and extension plates may be attached via an adhesive in an alternative embodiment.

The main body 206 and the lower surface 210 cooperatively define an engaging recess 260. The engaging recess 260 is configured to engage a portion of another plate, such as a plate that has already been implanted in a body (described below). A particular example of a plate that the engaging recess 206 is configured to engage is described in U.S. patent application Ser. No. 14/502,721, the contents of which is expressly incorporated by reference. In use, for example, the engaging recess 260 of the connecting plate 200 is placed over a portion of one of the plates described in U.S. patent application Ser. No. 14/502,721 such that the anchor passageways 220, 222 and locking member passageways 250, 252 align and allow for at least one anchor (described below) to be disposed through one of the anchor passageways 220, 222 of the connecting plate 200 and one of the anchor passageways of the previously-implanted plate, respectively, and at least one locking member (described below) to be disposed through one of the locking member passageways 250, 252 of the connecting plate 200 and one of the locking member passageways of the previously-implanted plate, respectively. A skilled artisan will be able to determine other plates that the engaging recess may engage with and also will be able to customize the engaging recess to engage a number of other plates based on various considerations, including the shapes and sizes of the plates to which the connecting member is to be attached to and the intended location at which the particular vertebral plate revision apparatus will be implanted. In an alternative embodiment, the engaging recess may be configured to engage a plate or portion of a plate that is circular, elliptical, triangular, rectangular, or any other shape and a plate that is not described in the aforementioned patent application. Additionally, in other embodiments, multiple anchors may be inserted through the anchor passageways of either or both of the anchor passageways defined by the connecting plate and the anchor passageways defined by the previously-implanted plate and multiple locking members may be inserted through the locking member passageways defined by one or both of the connecting plate and the extension plate.

As best illustrated in FIG. 4, in this embodiment the engaging recess 260 is comprised of a base 262, a side 264, and four flanges 265a, 265b, 265c, 265d. The side 264 is adjacent each of the base 262 and the lower surface 222. The base 262 defines the lower openings 225, 227 of the respective first and second anchor passageways 220, 222, as well as the lower openings 255, 257 of the locking member passageways 250, 252. The first and second flanges 265a, 265b are disposed adjacent the lower opening 225 of one of the anchor passageways 220 and the third and fourth flanges 265c, 265d are disposed adjacent the lower opening 227 of the other anchor passageway 222. Each of the flanges 265a, 265b, 265c, 265d is defined by a gap 266a, 266b, 266c, 266d defined by the base 262. Each of the flanges 265a, 265b, 265c, 265d is configured such that the engagement of another plate (described below) repositions the flanges 265a, 265b, 265c, 265d as the connecting plate 200 is engaging the other plate. Upon complete engagement of the other plate by the connecting plate 200, however, the flanges 265a, 265b, 265c, 265d return to their original configuration and act as a secondary method of locking the connecting member 200 and the other plate together. A skilled artisan will be able to determine whether to include flanges, how many flanges to include, and how best to configure the flanges based on various considerations, including the shapes and sizes of the plates to which the connecting member is to be attached to and the intended location at which the particular vertebral plate revision apparatus will be implanted. In another embodiment, the base does not define any flanges. In different embodiments, the base may define one, two, three, five, or more than five flanges. Though the flanges 265a, 265b, 265c, 265d are substantially rectangular in the illustrated embodiment, in other embodiments the flanges may be circular, rectangular, triangular, elliptical, or any other shape. Additionally, each of the flanges may be comprised of the same material as the rest of the connecting plate, or a different material than the rest of the connecting plate.

The vertebral plate revision apparatus 10 also includes a connecting member 300. The connecting member 300 has a proximal end 302, a distal end 304, a main body 306 extending from the proximal end 302 to the distal end 306, an upper surface 308, a lower surface 310, a channel 314 extending from the upper surface 308 to the lower surface 310, a side 312 extending from the upper surface 308 to the lower surface 310, and an indented ring 316 defined by the upper surface 310.

In the illustrated embodiment, each of the upper and lower surface 308, 310 is hexagonal in shape. The upper and lower surfaces 308, 310 may have other shapes, however. A skilled artisan will be able to determine suitable shapes for the upper and lower surfaces based on various considerations, including the size and shapes of the connecting plate and the extension plate. Examples of suitable upper and lower surface shapes include circular, triangular, rectangular, elliptical, or any other shape. Furthermore, the upper surface may be shaped differently than the lower surface in alternative embodiments.

The side 312 is comprised of six panels 320a, 320b, 320c, 320d, 320e, 320f. Each of the panels 320a, 320b, 320c, 320d, 320e, 320f is substantially rectangular in shape and is the same size and shape as each other panel 320a, 320b, 320c, 320d, 320e, 320f. Each of the panels 320a, 320b, 320c, 320d, 320e, 320f may have other shapes and sizes, however. A skilled artisan will be able to determine suitable shapes and sizes for the panels based on various considerations, including the size and shapes of the connecting plate and the extension plate. Examples of suitable panel shapes include circular, triangular, rectangular, elliptical, or any other shape. Furthermore, the any single panel may be sized and shaped differently than any other single panel. The side may comprise one, two, three, four, five, seven, or more than seven panels in other embodiments, as well.

The main body 306 defines a channel 314 extending from the upper surface 308 to the lower surface 310 that is circular in shape. The channel 314 also has an eleventh diameter $d_{11}$ and an inner surface 330. The eleventh diameter is greater than the diameter (not illustrated) of the tip 244 of the connecting member boss 240 and substantially equal to the diameter (not illustrated) of the connecting member passageway 140. The inner surface 330 defines a threaded portion 332 configured to mate with the threads 248 of the connecting member boss 240. A skilled artisan will be able to determine suitable shapes for the channel and a suitable eleventh diameter based on various considerations, including the size and shapes of the connecting plate and the extension plate. Examples of suitable channel shapes include circular, triangular, rectangular, elliptical, or any other shape. Additionally, the eleventh diameter may be greater than or less than the diameter of the connecting member passageway in other embodiments.

Figure 2:
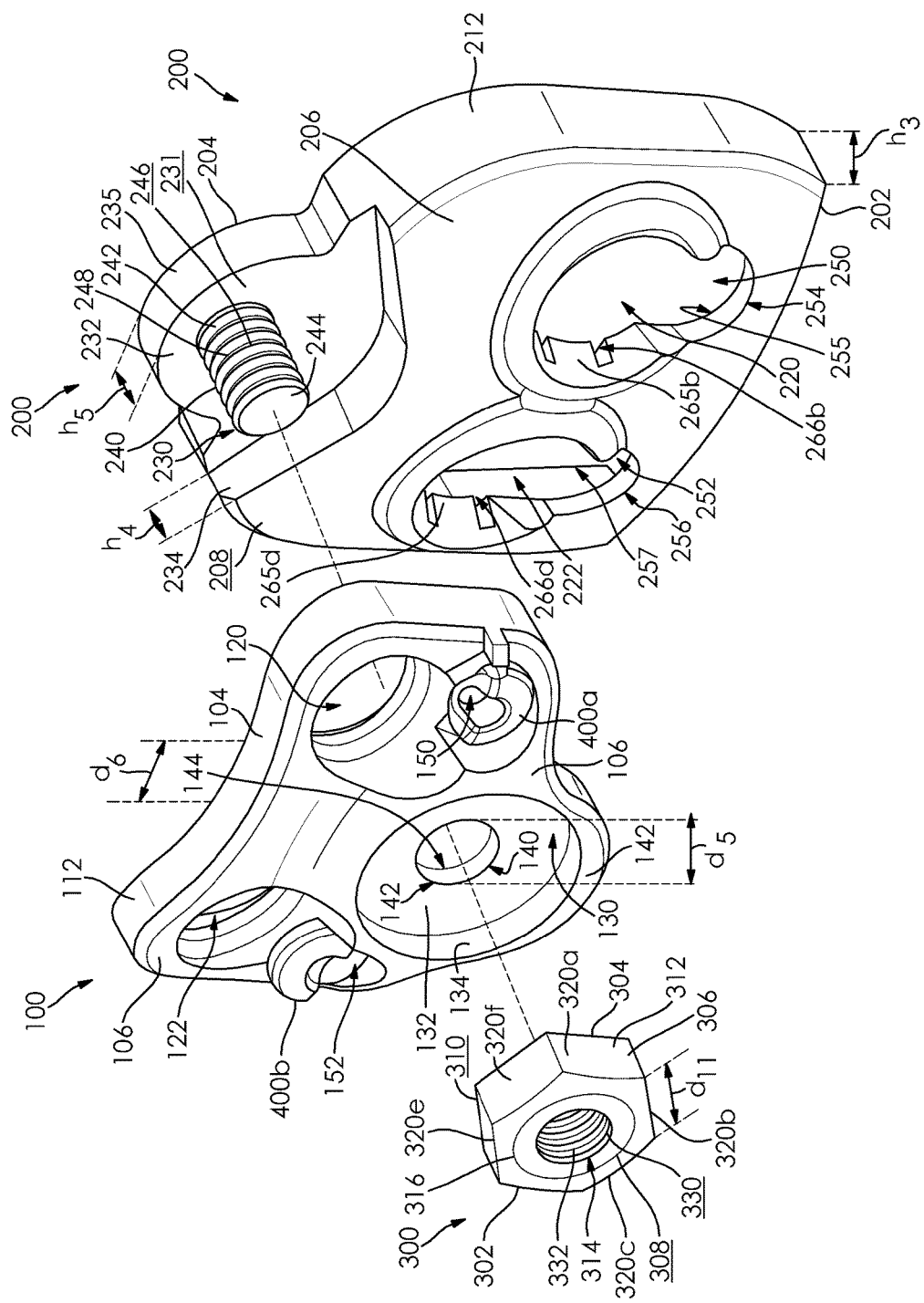
FIG. 2 is an exploded view of the vertebral plate revision apparatus illustrated in FIG. 1.
Figure 3:
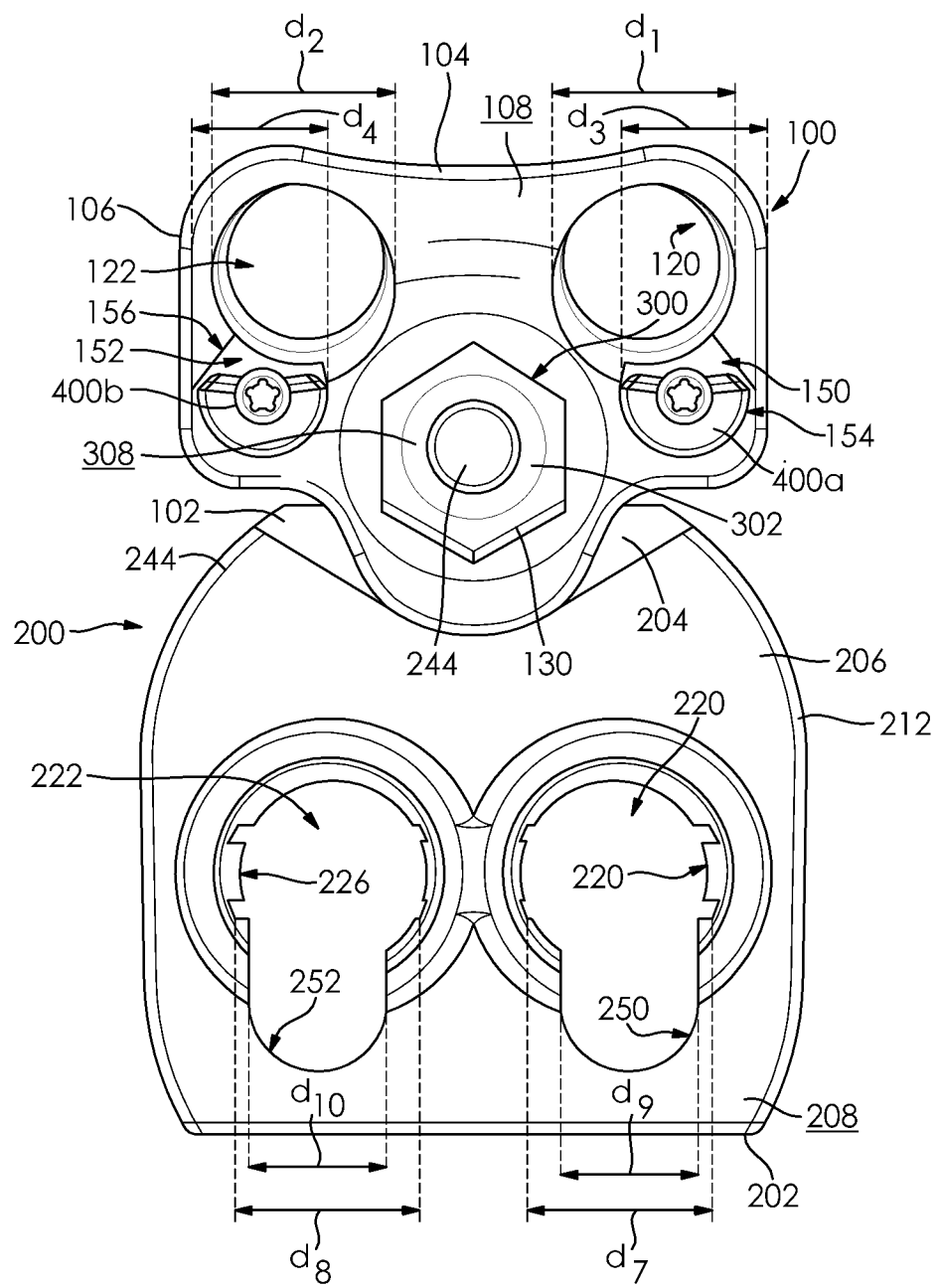
FIG. 3 is a top view of the vertebral plate revision apparatus illustrated in FIG. 1.

In use, and described below and best illustrated in FIG. 2, the connecting member boss 240 is disposed through the connecting member passageway such that the tip 244 is disposed through the connecting member upper passageway opening 142. The threaded portion 332 of the connecting member 300 then mates with the threads 248 of the connecting member boss 240 as the connecting member boss 240 is rotatably attached to the connecting member 300. The connecting member 300 may be attached to the connecting member boss 240 manually or via a driver (not illustrated in the Figures). Such a driver would engage the indented ring 314 defined by the upper surface 308 such that rotational movement of the driver would rotate the connecting member 300 and locking the connecting member 300, extension plate 100, and connecting plate 200 together. A skilled artisan will be able to determine whether to manually attach the connecting member, extension plate, and connecting plate, or whether a tool is desirable for doing so. In another embodiment, the tool may engage the sides of the connecting member, rather than the indented ring. In a different embodiment, the indented ring may not be defined by the upper surface. Though the connecting member comprises a nut in the illustrated embodiment, in other embodiments a screw, pin, rod, rivet, or any other mechanical attachment may be used in place of the nut.

The illustrated embodiment also includes locking members 400a, 400b disposed in the locking member passageways 150, 152 of the extension plate 100. The locking members 400a, 400b described above and illustrated in FIGS. 1 through 6 are described in U.S. patent application Ser. No. 14/502,721. A skilled artisan will be able to determine other locking members that may engage the extension plate based on various considerations, including the size and shape of the anchors that are disposed within the anchor passageways and the intended location at which the particular vertebral plate revision apparatus will be implanted. In an alternative embodiment, no locking members may be included. In a different embodiment, the locking members may be locking members other than those described in U.S. patent application Ser. No. 14/502,721. Any suitable locking member may be used in alternative embodiments.

Figure 7:
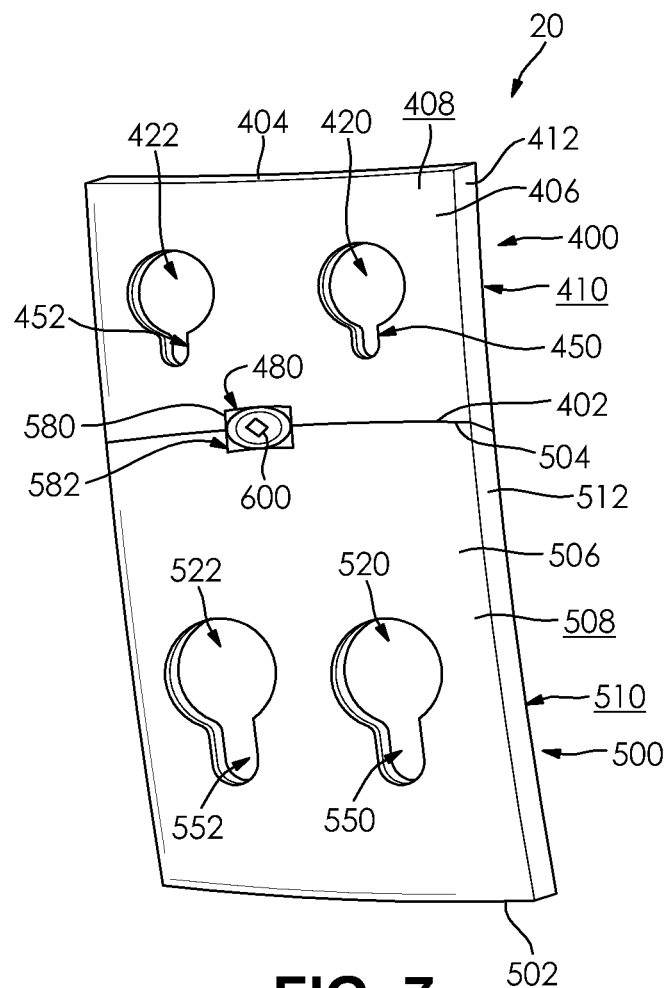
FIG. 7 is a perspective view of another vertebral plate revision apparatus.

FIG. 7 illustrates another example vertebral plate revision apparatus 20. This example vertebral plate revision apparatus 20 includes an extension plate 400, a connecting plate 500, and a connecting member 600.

The extension plate 400 comprises a proximal end 402, a distal end 404, a main body 406 extending from the proximal end 402 to the distal end 404, an upper surface 408, a lower surface 410, a side 412 extending from the upper surface 408 to the lower surface 410, a set of anchor passageways 420, 422, a set of locking member passageways 450, 452, and a channel 480 disposed on the proximal end 402 that is cooperatively defined by the upper surface 408 and the lower surface 410.

The connecting plate 500 comprises a proximal end 502, a distal end 504, a main body 506 extending from the proximal end 502 to the distal end 504, an upper surface 508, a lower surface 510, a side 512 extending from the upper surface 508 to the lower surface 510, a set of anchor passageways 520, 522, a set of locking member passageways 550, 552, and an extension 580 defining a channel 582 disposed on the distal end 504 cooperatively defined by the upper surface 508, the lower surface 510, and the side 512.

The connecting member 600 has a proximal end 602, a distal end 604, a main body 606 extending from the proximal end 602 to the distal end 606, an upper surface 608, a lower surface 610, and a side 612 extending from the upper surface 608 to the lower surface 610. The connecting member 600 attaches the connecting plate 500 to the extension plate 400.

Figure 8:
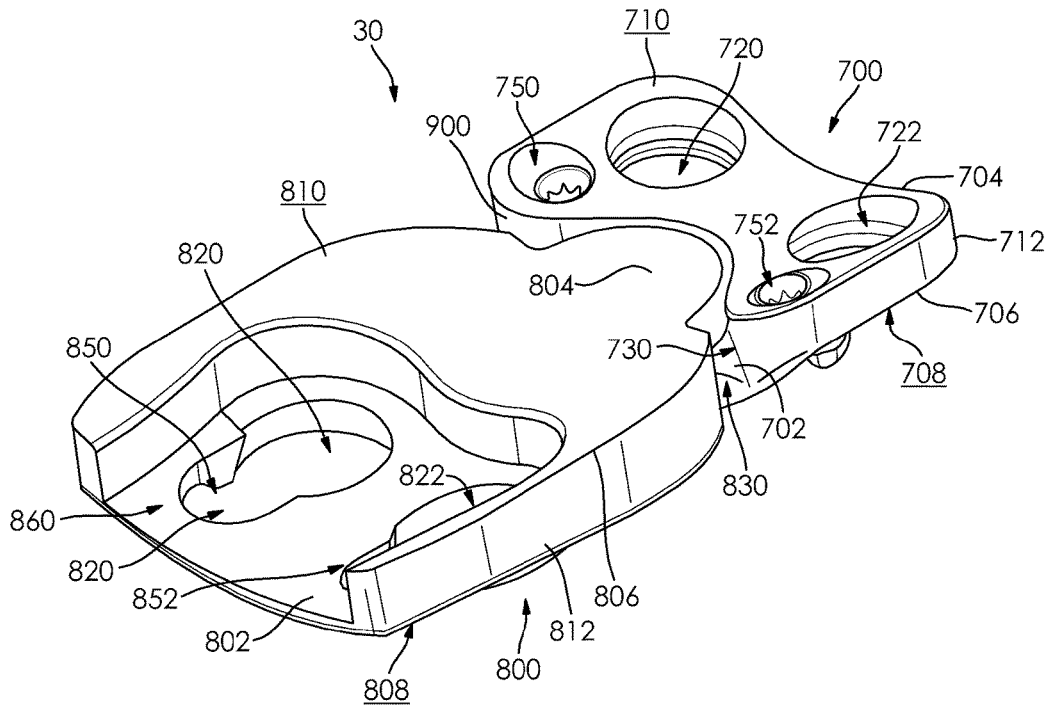
FIG. 8 is a perspective view of another vertebral plate revision apparatus.

FIG. 8 illustrates another example vertebral plate revision apparatus 30. This example vertebral plate revision apparatus 30 includes an extension plate 700, a connecting plate 800, and a connecting member 900.

The extension plate 700 comprises a proximal end 702, a distal end 704, a main body 706 extending from the proximal end 702 to the distal end 704, an upper surface 708, a lower surface 710, a side 712 extending from the upper surface 708 to the lower surface 710, a set of anchor passageways 720, 722, a connecting member recess 730, a connecting member passageway (not illustrated in the Figures), and a set of locking member passageways 750, 752.

The connecting plate 800 comprises a proximal end 802, a distal end 804, a main body 806 extending from the proximal end 802 to the distal end 804, an upper surface 808, a lower surface 810, a side 812 extending from the upper surface 808 to the lower surface 810, a set of anchor passageways 820, 822, a connecting member recess 830, a connecting member passageway (not illustrated in the Figures), a set of locking member passageways 850, 852, and an engaging recess 860.

The connecting member (not illustrated in the Figures) has a proximal end, a distal end, a main body extending from the proximal end to the distal end, an upper surface, a lower surface, and a side extending from the upper surface to the lower surface (not illustrated in the Figures). The connecting member attaches the connecting plate 700 to the extension plate 800.

Figure 9:
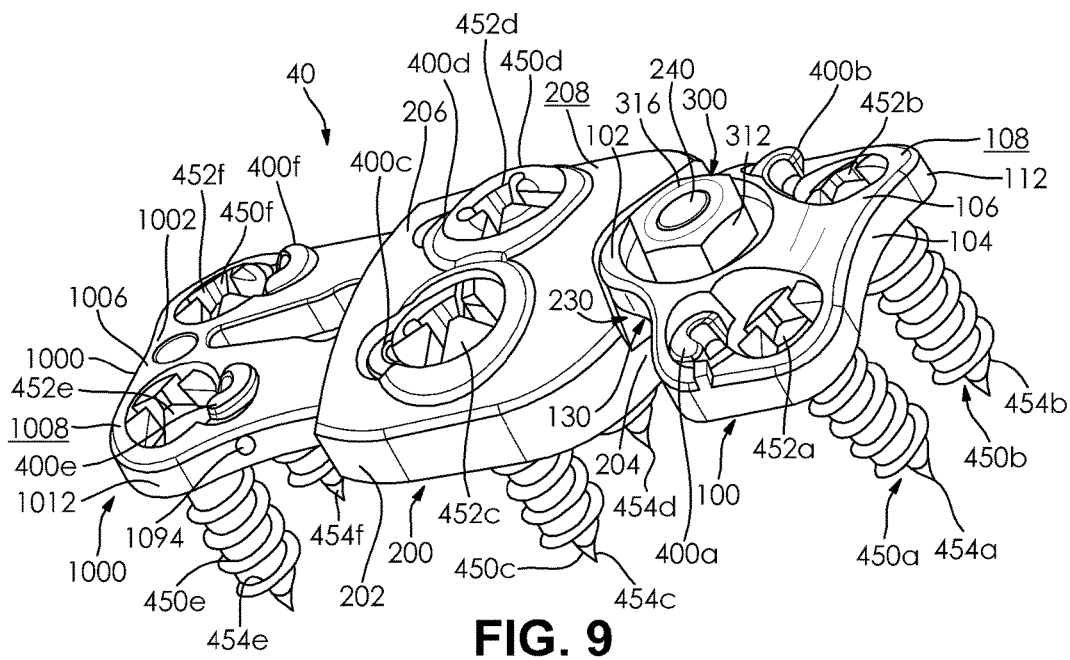
FIG. 9 is a perspective view of an osteosynthesis system.

Each of FIGS. 9, 10, 11, 12, and 13 illustrates an osteosynthesis system 40 or a component or components thereof. FIG. 9 illustrates an extension plate 100, a connecting plate 200, a connecting member 300, a previously-implanted plate 1000, and a set of anchors 450a, 450b, 450c, 450d, 450e, 450f.

Each of the extension plate 100, connecting plate 200, and connecting member 300 is described above and illustrated in FIGS. 1 through 6. Thus, the extension plate 100 comprises a proximal end 102, a distal end 104, a main body 106 extending from the proximal end 102 to the distal end 104, an upper surface 108, a lower surface 110, a side 112 extending from the upper surface 108 to the lower surface 110, a set of anchor passageways 120, 122, a connecting member recess 130, a connecting member passageway (not illustrated in FIGS. 9 through 13), and a set of locking member passageways 150, 152. The connecting plate 200 comprises a proximal end 202, a distal end 204, a main body 206 extending from the proximal end 202 to the distal end 204, an upper surface 208, a lower surface 210, a side 212 extending from the upper surface 208 to the lower surface 210, a set of anchor passageways 220, 222, a connecting member recess 230, a connecting member boss 240, a set of locking member passageways 250, 252, and an engaging recess 260. The connecting member 300 comprises a proximal end 302, a distal end 304, a main body 306 extending from the proximal end 302 to the distal end 306, an upper surface 308, a lower surface 310, a channel 314 extending from the upper surface 308 to the lower surface 310, a side 312 extending from the upper surface 308 to the lower surface 310, and an indented ring 316 defined by the upper surface 310.

Any previously-implanted plate may be used in conjunction with the extension plate 100, connecting plate 200, and connecting member 300. In the illustrated embodiment, the previously-implanted plate 1000 comprises the plate that is illustrated and described in U.S. patent application Ser. No. 14/502,721. More specifically, the plate illustrated, for example, in FIGS. 1, 2, 3, and 4 is described and illustrated herein. Therefore, the previously-implanted plate 1000 comprises a proximal end 1002, a distal end 1004, a main body 1006 extending from the proximal end 1002 to the distal end 1004, an upper surface 1008, a lower surface 1010, a side 1012 extending from the upper surface 1008 to the lower surface 1010, a set of anchor passageways 1020, 1022, 1024, 1026, a set of locking member passageways 1050, 1052, 1054, 1056, a set of pin passageways (not illustrated in the Figures), a set of pins 1090, 1092, 1094, 1096 disposed within the respective pin passageways, and a set of locking members 400c, 400d, 400e, 400f disposed within the set of locking member passageways 1050, 1052, 1054, 1056, respectively. A skilled artisan will be able to determine a suitable plate for use in conjunction with the vertebral plate revision apparatus based on various considerations, including the size and shape of the anchors that will be disposed within the anchor passageways and the intended location at which the particular vertebral plate revision apparatus will be implanted. In another embodiment, the vertebral plate revision apparatus may be used in conjunction with a plate that has not been previously-implanted. Other suitable plates may have zero, one, two, three, five, or more than five anchor passageways in alternative embodiments and may be shaped and sized in any way.

Figure 10:
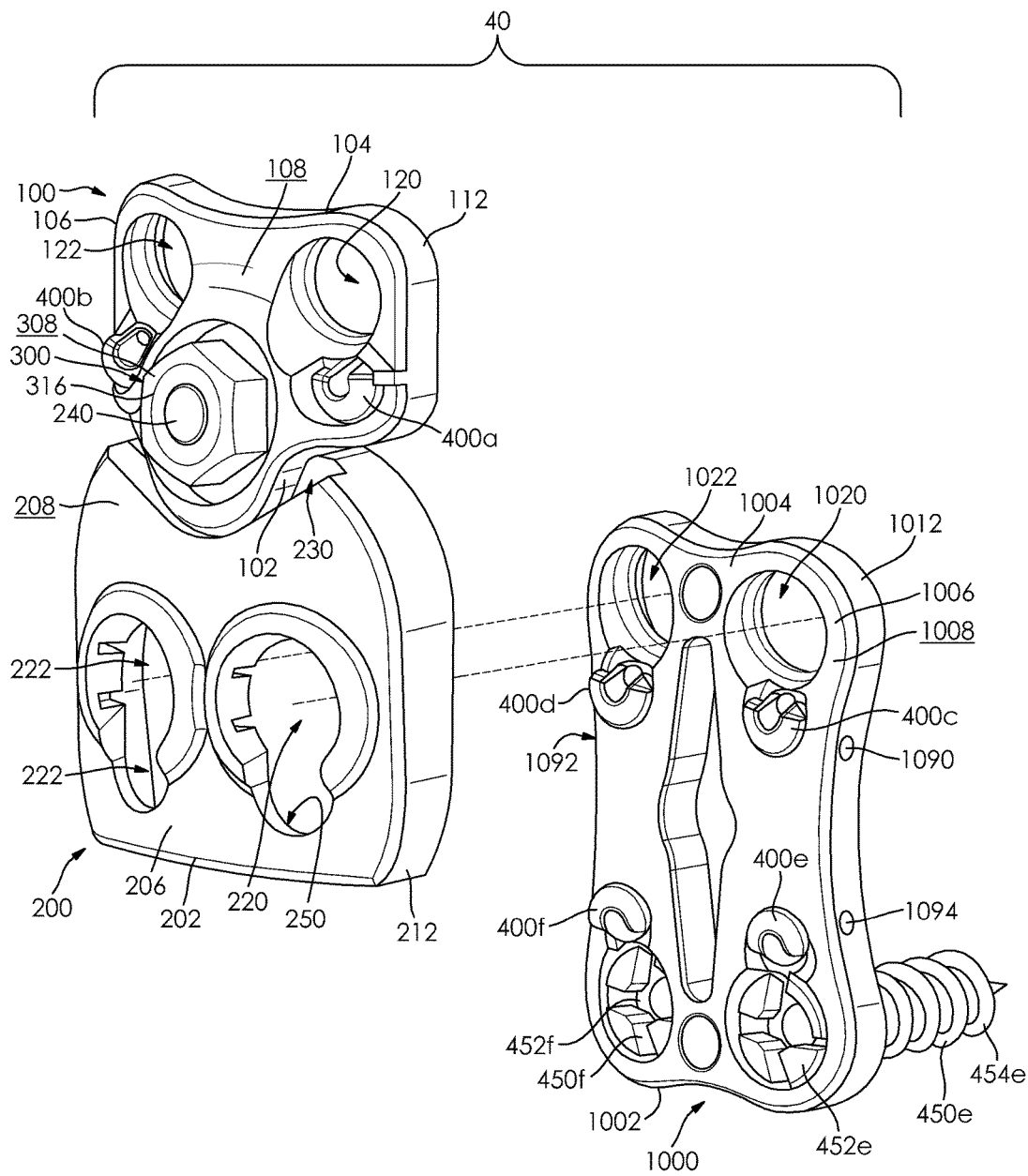
FIG. 10 is an exploded view of the osteosynthesis system illustrated in FIG. 9. Four of the anchors illustrated in FIG. 9 are not shown.
Figure 11:
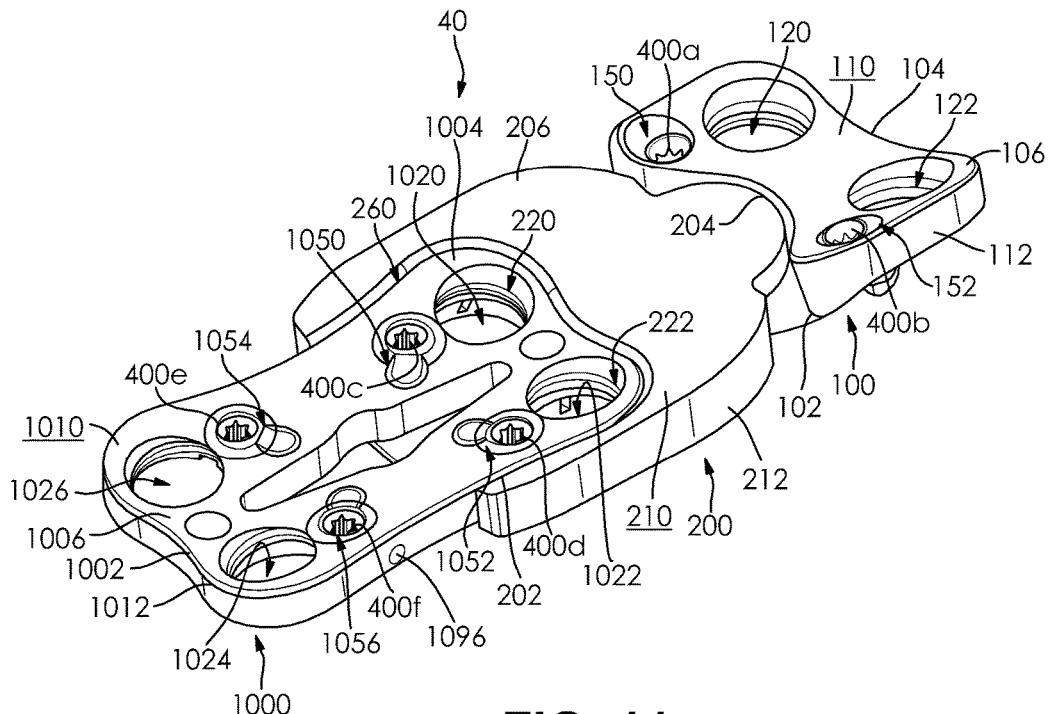
FIG. 11 is a perspective view of the osteosynthesis system illustrated in FIG. 9. The anchors illustrated in FIG. 9 are not shown.
Figure 12:
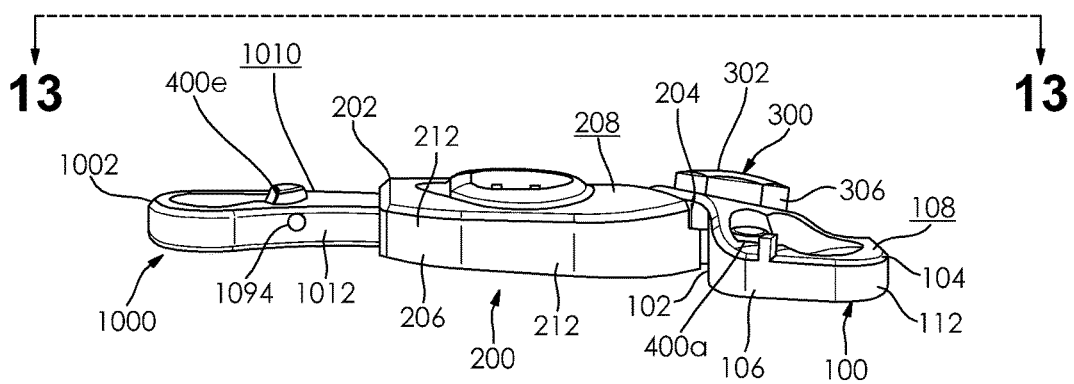
FIG. 12 is a side view of the osteosynthesis system illustrated in FIG. 11.
Figure 13:
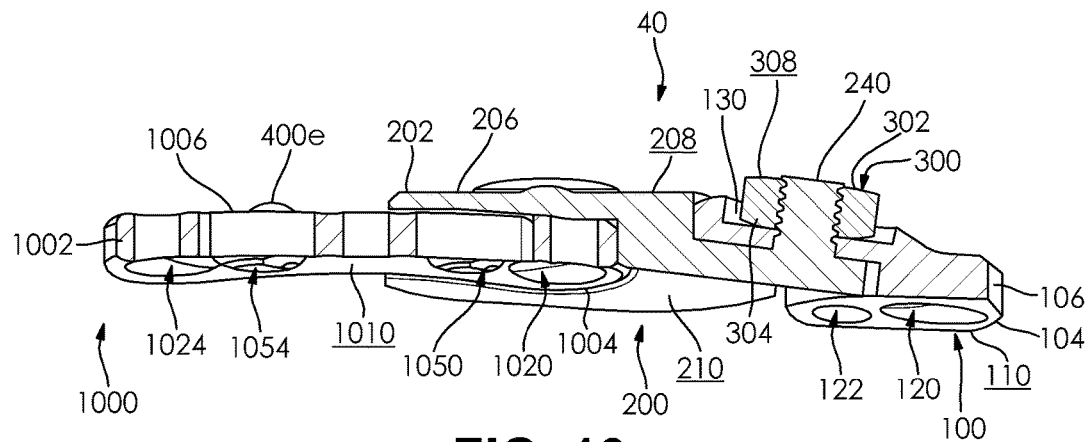
FIG. 13 is a sectional view of the osteosynthesis system illustrated in FIG. 12, taken along line 13-13.
Figure 14:
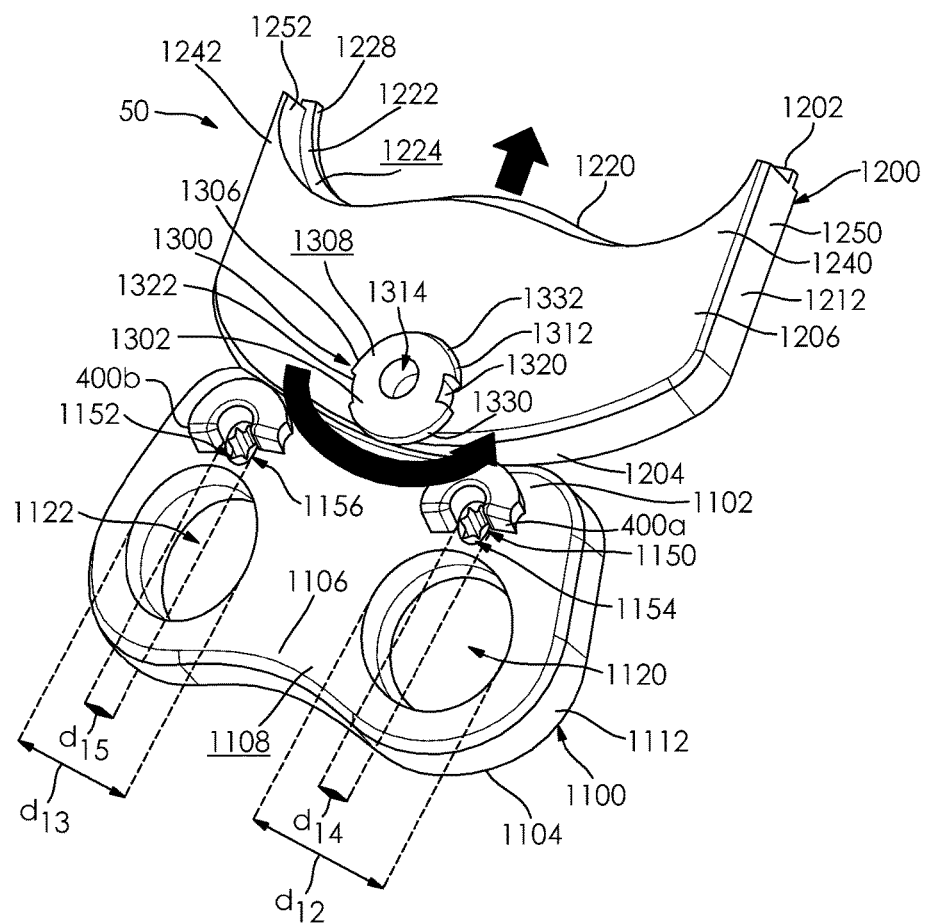
FIG. 14 is a perspective view of another vertebral plate revision apparatus.
Figure 15:
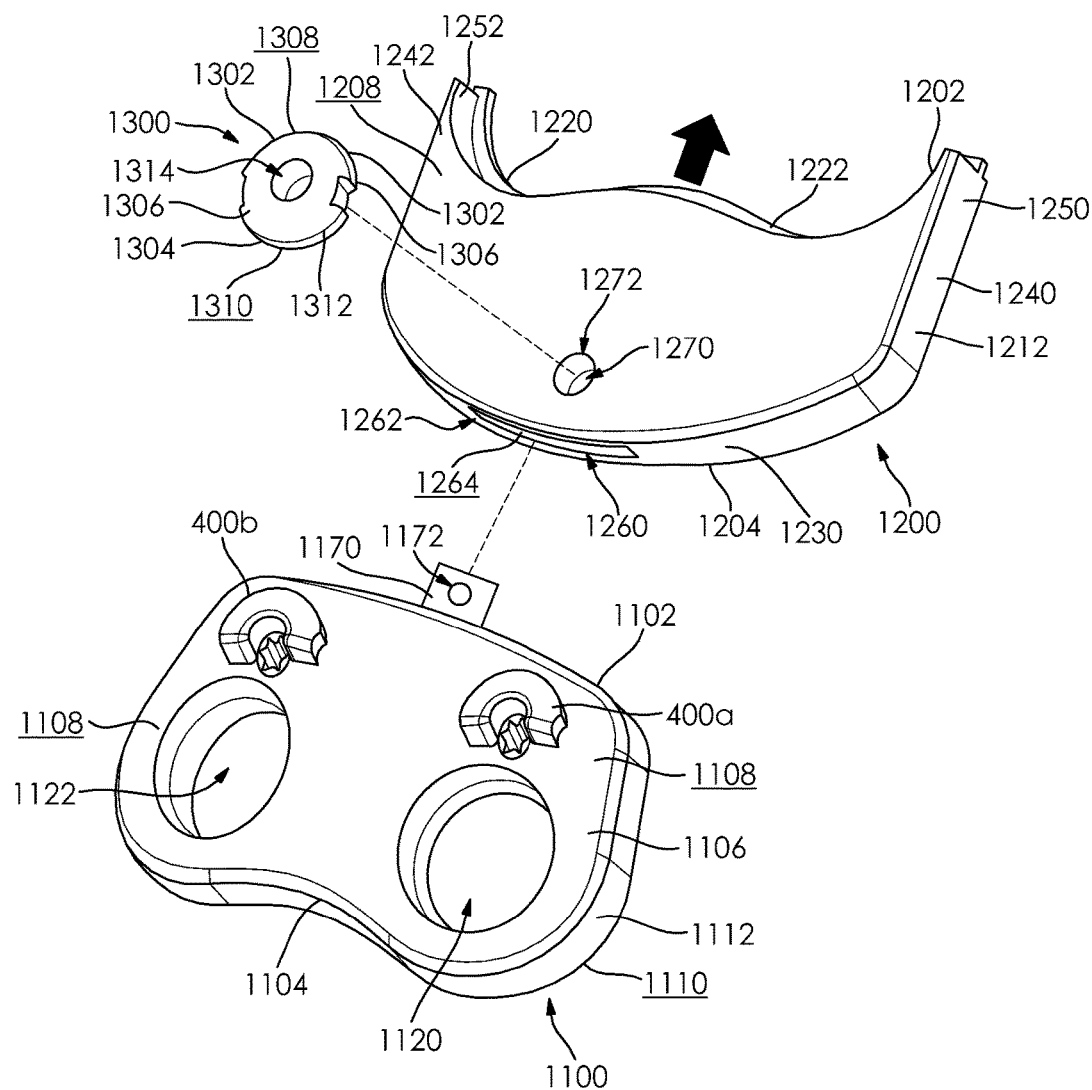
FIG. 15 is an exploded view of the vertebral plate revision apparatus illustrated in FIG. 14.
Figure 16:
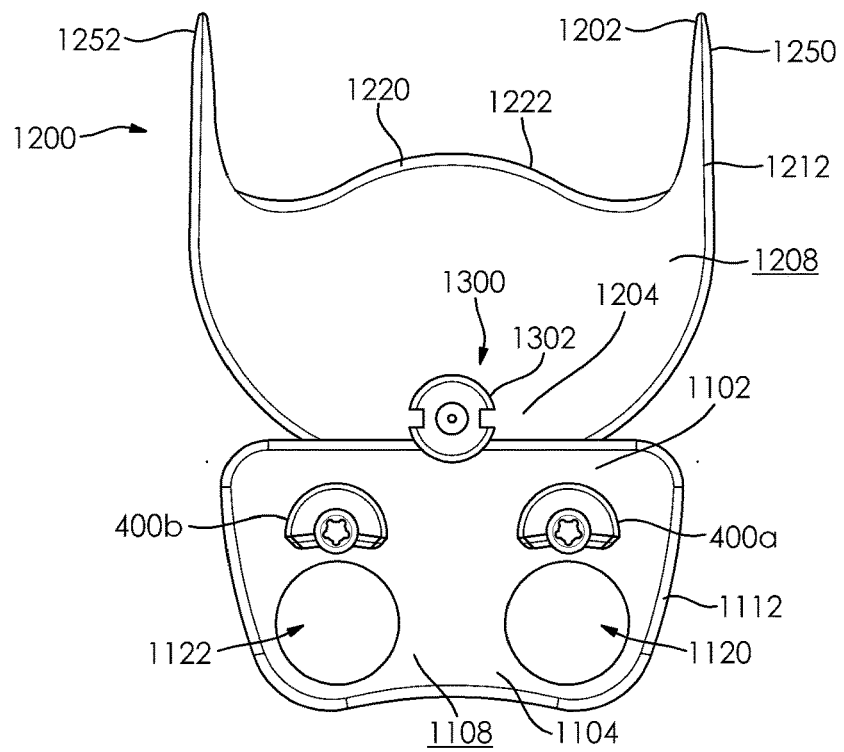
FIG. 16 is a top view of the vertebral plate revision apparatus illustrated in FIG. 14.
Figure 17:
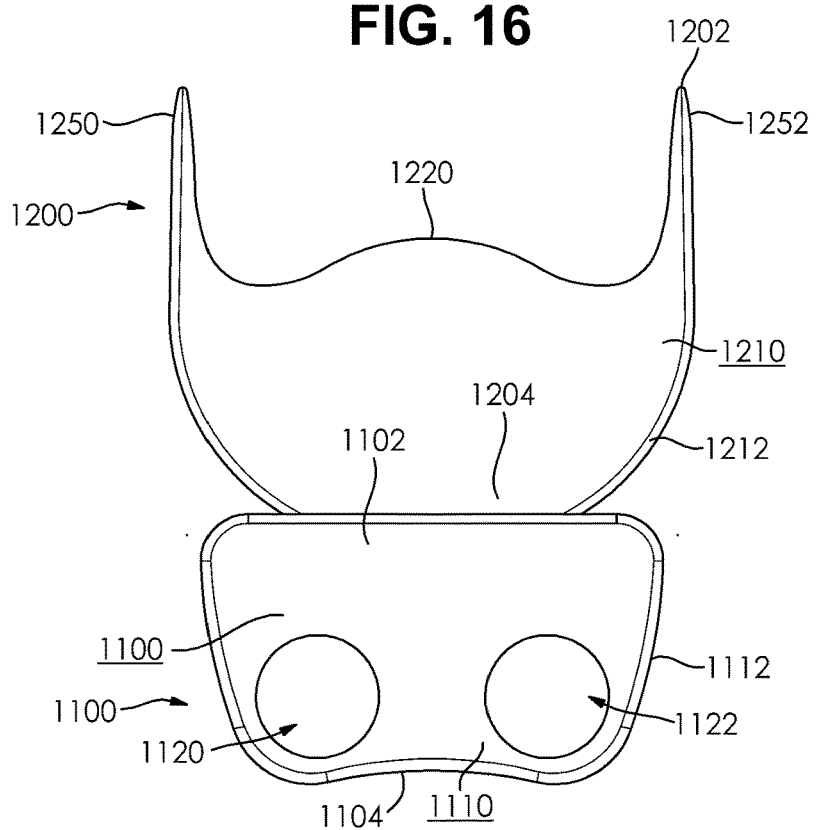
FIG. 17 is a bottom view of the vertebral plate revision apparatus illustrated in FIG. 14.
Figure 18:
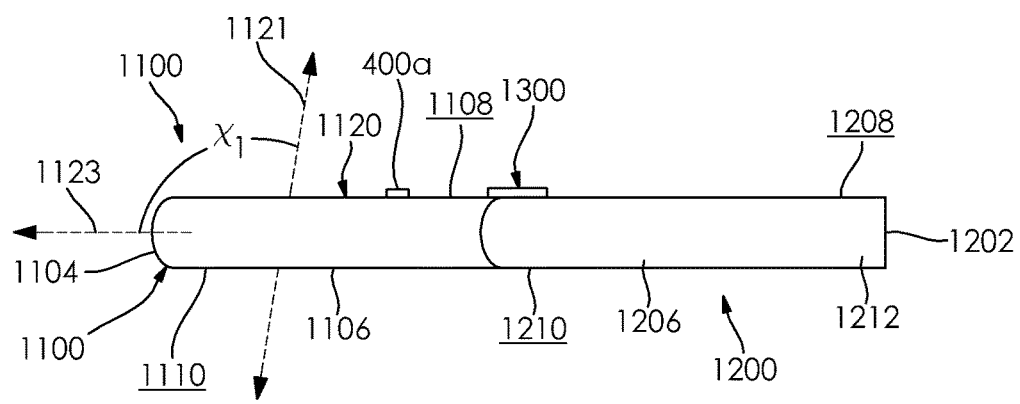
FIG. 18 is a side view of the vertebral plate revision apparatus illustrated in FIG. 14.

As best illustrated in FIGS. 10 and 11, once the extension plate 100, the connecting plate 200, the connecting member 300, and the first and second locking members 400a, 400b have been assembled, as described above, the connecting plate 200 engages the previously-implanted plate 1000. More specifically, the engaging recess 260 of the connecting plate 200 engages the upper surface 1008 and side 1012 of the previously-implanted plate 1000. As discussed above, the engaging recess 260 has been fitted to firmly engage the previously-implanted plate 1000. In the illustrated embodiment, the distal end 1004 of the previously-implanted plate 1000 engages the engaging recess 260. Furthermore, the connecting plate 200 engages the previously-implanted plate 1000 such that its anchor passageways 220, 222 and the locking member passageways 250, 252 are substantially aligned with the anchor passageways 1020, 1022 and locking member passageways 1050, 1052 of the previously-implanted plate 1000, respectively. A skilled artisan will be able to determine how best to engage the connecting plate with the previously-implanted plate based on various considerations, including the size and shape of the anchors that are disposed within the anchor passageways and the intended location at which the particular vertebral plate revision apparatus will be implanted. In a different embodiment, the connecting plate may engage the proximal end of the previously-implanted plate. In another embodiment, the connecting plate and previously-implanted plate may engage one another, but not be positioned such that their respective anchor passageways and locking member passageways are aligned. Alternatively, the connecting plate may be placed under yet still engage the previously-implanted plate in other embodiments.

As best illustrated in FIG. 9, when the connecting plate 200 of the vertebral plate revision apparatus 10 has engaged the previously-implanted plate 1000, one or more anchors 450a, 450b, 450c, 450d, 450e, 450f may be disposed through the anchor passageways 120, 122 of the extension plate, the anchor passageways 220, 222 of the connecting plate 200, and the anchor passageways 1020, 1020, 1024, 1026 of the previously-implanted plate 1000. In this example, the anchors 450a, 450b, 450c, 450d, 450e, 450f comprise the anchors described and illustrated in U.S. patent application Ser. No. 14/502,721 to Craig Black for OSTEOSYNTHE- SIS SYSTEM, ASSEMBLIES AND COMPONENTS, the entire contents of which are expressly incorporated into this disclosure for the purpose of describing suitable anchors for use in an osteosynthesis system. Any suitable anchor or set of anchors may be used, however. Each of the anchors 450a, 450b, 450c, 450d, 450e, 450f has a head 452a, 452b, 452c, 452d, 452e, 452f and a shaft 454a, 454b, 454c, 454d, 454e, 454f. The shafts 454a, 454b, 454c, 454d, 454e, 454f are disposed through the first anchor passageway 120, the second anchor passageway 122, the first anchor passageway 220 and the first anchor passageway 1020, the second anchor passageway 222 and the second anchor passageway 1022, the third anchor passageway 1024, and the fourth anchor passageway 1024, respectively, such that they can engage a bone or portion of a bone. The anchors 450a, 450b, 450c, 450d, 450e, 450f engage their respective adjacent locking members 400a, 400b, 400c, 400d, 400e, 400f. A skilled artisan will be able to determine how many anchors to include and the type of anchor that to use based on various considerations, including the intended location at which the particular vertebral plate revision apparatus will be implanted. In a different embodiment, zero, one, two, three, four, five, seven, or more than seven anchors may be included. In another embodiment, the anchors may comprise one or more of the anchors illustrated in the Figures, and one or more of a different type of anchor, or a set of anchors completely different than those described above. In alternative embodiments, more than one anchor may be disposed in a single anchor passageway. Alternatively, a single locking member may engage more than one anchor.

Each of FIGS. 14, 15, 16, 17, and 18 illustrates another example vertebral revision apparatus 50. The vertebral plate revision apparatus 50 includes an extension plate 1100, a connecting plate 1200, a connecting member 1300, and a set of locking members 400a, 400b.

The extension plate 1100 comprises a proximal end 1102, a distal end 1104, a main body 1106 extending from the proximal end 1102 to the distal end 1104, an upper surface 1108, a lower surface 1110, a side 1112 extending from the upper surface 1108 to the lower surface 1110, a set of anchor passageways 1120, 1122, a set of locking member passageways 1150, 1152, and an extension piece 1170 extending from the side 1112.

In the illustrated embodiment, each of the anchor passageways 1120, 1122 extends from the upper surface 1108 to the lower surface 1110 of the main body 1106. Each of the anchor passageways 1120, 1122 has a central axis that lies on a plane that is disposed at an angle to a plane that contains a central longitudinal axis of the extension plate 1100. For example, the first anchor passageway 1120 has a central axis that lies on a first plane 1121, which is disposed at a first angle $\chi_1$ to a second plane 1123, which contains the central longitudinal axis of the main body 1106 of the extension plate 1100. Similarly, the second anchor passageway 1122 has a central axis that lies on a third plane (not illustrated in the Figures), which is disposed at a second angle (not illustrated in the Figures) to the second plane 1123, which contains the central longitudinal axis of the main body 1106 of the extension plate 1100. This configuration places anchors (such as one of anchors 450a, 450b, 450c, 450d, 450e, 450f) disposed within the anchor passageways 1120, 1122 at an angle to the second plane 1123 that contains central longitudinal axis of the main body 1106 of the extension plate 1100. The anchor passageways 1120, 1122 can be disposed at any suitable angle, and a skilled artisan will be able to select appropriate angles according to a particular embodiment based on various considerations, including the intended use and location at which the particular vertebral plate revision apparatus will be implanted. In this embodiment, the first and second anchor passageways 1120, 1122 are disposed on one end of the extension plate 1100 and the first and second anchor passageways 1120, 1122 are configured such that the first angle $\chi_1$ is inverse to the second angle (not illustrated in the Figures) relative to the second plane 1123. For example, the first angle can be between about 10° and about 90°, between about 25° and about 75°, and between about 40° and about 60° in various embodiments. The second angle can be between about −10° and about −90°, between about −25° and about −75°, and between about −40° and about −60° in various embodiments, as well. It is noted, though, that different angles can be used and, indeed, each of the anchor passageways in a vertebral plate revision apparatus according to a particular embodiment can be disposed at an angle that is different from one, more than one, or all of the anchor passageways defined by the plates of the particular vertebral plate revision apparatus.

The first and second anchor passageways 1120, 1122 define twelfth and thirteenth diameters $d_{12}$, $d_{13}$, respectively. In the illustrated embodiment, the twelfth diameter $d_{12}$ is equal to the thirteenth diameter $d_{13}$. A skilled artisan will be able to determine suitable twelfth and thirteenth diameters based on various considerations, including the intended use and location at which the particular vertebral plate revision apparatus will be implanted. In an alternative embodiment, the twelfth diameter may be less than the thirteenth diameter. In a different embodiment, the twelfth diameter may be greater than or about equal to the thirteenth diameter.

The main body 1106 also defines locking member passageways 1150, 1152, which respectively define locking member openings 1154 and 1156. Each locking member passageway 1150, 1152 extends from the upper surface 1108 to the lower surface 1110. Each of the locking member passageways 1150, 1152 has an upper portion (not illustrated in the Figures) and a lower portion (not illustrated in the Figures). For each of the locking member passageways 1150, 1152, the upper portion is adjacent one of the anchor passageways 1120, 1122. Additionally, the lower portions of the locking member passageways 1120, 1122 are cylindrical in shape. The locking member passageways 1150, 1152 are configured to engage a locking member, such as the locking members 400a, 400b described above and illustrated in FIG. 14. A skilled artisan will be able to determine whether to include a set of locking member passageways, how many locking member passageways to include, and how best to configure the locking member passageways based on various considerations, including the intended use and location at which the particular vertebral plate revision apparatus will be implanted. In an alternative embodiment, the main body may define more than two locking member passageways. In a different embodiment, the entire locking member passageways may be in communication with their respective adjacent locking member passageways. In another embodiment, any portion of the locking member passageways, including the upper portion, lower portion, or both portions, may have any shape, including conical, cylindrical, or spherical.

The first and second locking member passageways 1150, 1152 define fourteenth and fifteenth diameters $d_{14}$, $d_{15}$, respectively. In the illustrated embodiment, the fourteenth diameter $d_{14}$ is equal to the fifteenth diameter $d_{15}$. Each of the fourteenth and fifteenth diameters $d_{14}$, $d_{15}$ is also less than each of the twelfth and thirteenth diameters $d_{12}$, $d_{13}$. The fourteenth and fifteenth diameters must, however, be great enough to allow for the first and second locking member passageways 1150, 1152 to engage the locking members 400a, 400b, respectively. A skilled artisan will be able to determine suitable fourteenth and fifteenth diameters based on various considerations, including the intended use and location at which the particular vertebral plate revision apparatus will be implanted. In an alternative embodiment, the fourteenth diameter may be less than the fifteenth diameter. In a different embodiment, the fourteenth diameter may be greater than or about equal to the fifteenth diameter.

In the illustrated embodiment, the extension piece 1170 extends from and is integrally formed with the side 1112 of the distal end 1104 of the extension plate 1100. The extension piece 1170 includes a channel 1172 extending from the upper surface 1174 to the lower surface 1176 of the extension piece 1170. The channel 1172 is cylindrical in the illustrated embodiment and is configured to engage the connecting member 1300 and be inserted into the slot of the connecting plate 1200 (described below). A skilled artisan will be able to determine how to configure the extension piece based on various considerations, including the intended use and location at which the particular vertebral plate revision apparatus will be implanted. In other embodiments, the extension piece may be threaded or define another mechanical attachment mechanism. In a different embodiment, the channel may be spherical, conical, pyramidal, or any other shape. Alternative, the extension piece may be configured to engage a portion of the connecting plate or be inserted into another portion of the connecting member rather than the slot, such as the upper or lower surface.

The connecting plate 1200 comprises a proximal end 1202, a distal end 1204, a main body 1206 extending from the proximal end 1202 to the distal end 1204, an upper surface 1208, a lower surface 1210, and a side 1212 extending from the upper surface 1208 to the lower surface 1210.

In the illustrated embodiment, the side 1212 includes a first portion 1220, a second portion 1230 substantially opposite the first portion 1220, and first and second lateral portions 1240, 1242. Each of the first and second lateral portions 1240, 1242 extends from the first portion 1220 to the second portion 1230. The first portion 1220 is disposed at the proximal end 1202 of the connecting plate 1200 and the second portion 1230 is disposed at the distal end 1204 of the connecting plate 1200. The first portion 1220 and the first lateral portion 1240 cooperatively define a first arm 1250 configured to engage another plate, such as previously-implanted plate 1000, described above. Similarly the first portion 1220 and the second lateral portion 1242 cooperatively define a second arm 1252 configured to engage another plate, such as previously-implanted plate 1000, described above. Each of the first and second arms 1250, 1252 are substantially similar in size and shape and extend toward the proximal end of a previously-implanted plate. A skilled artisan will be able to determine how best to shape the extension plate and whether to include arms based on various considerations, including the intended use and location at which the particular vertebral plate revision apparatus will be implanted. In other embodiments, the extension plate may include zero, one, three, or more than three arms. In a different embodiment the first arm may be larger than the second arm. In a different embodiment, the first arm may be shaped differently than the second arm. Additionally, in other embodiments, the first portion may extend under the entire previously-implanted plate or any portion of the previously-implanted plate, or may not extend under the previously-implanted plate at all. Alternatively, the first portion may extend under an entire plate that has not been implanted or any portion of a plate that has not been implanted, or may not extend under the a plate that has not been implanted at all. In all embodiments, any portion of the connecting plate, including the first portion, may extend over a portion of or the entire previously-implanted plate.

The first portion 1220 also defines a lip 1222. The lip 1222 is configured to engage the lower surface and side of another plate, such as previously-implanted plate 1000, described above. The lip 1222 is configured such that the lower surface 1010 of the previously-implanted plate 1000 rests on its surface 1224 and such that the side 1012 of the previously-implanted plate 1000 is in contact with the wall 1228 of the lip 1222. Additionally, the lip 1222 may rise to any height relative to the first portion 1220. A skilled artisan will be able to determine whether to include a lip and how best to configure the lip based on various considerations, including the shape and size of the plate that the connecting member will engage and the location at which the particular vertebral plate revision apparatus will be implanted. In other embodiments, the lip may be rounded rectangular, pyramidal, cylindrical, triangular, elliptical, or any other shape. In a different embodiment, the lip may be configured such that it will contact the side and upper surface of the plate that it will engage, will contact only the upper surface of the plate, or will only contact the side of the plate. Additionally, in other embodiments, the lip may extend under the entire previously-implanted plate or any portion of the previously-implanted plate, or may not extend under the previously-implanted plate at all. In alternative embodiments, the lip may extend under an entire plate that has not been implanted or any portion of a plate that has not been implanted, or may not extend under the a plate that has not been implanted at all. In all embodiments, any portion of the lip may extend over or under a portion of or the entire previously-implanted plate.

The second portion 1230 of the side 1212 defines a slot 1260. The slot 1260 is disposed on the distal end 1204 of the connecting member 1200 and extends towards the proximal end 1202; it also includes a slot opening 1262 that is substantially rectangular in shape. The slot 1260 is configured such that it may mate with and house the extension piece 1170 of the extension plate 1100. The upper surface 1264 of the slot 1200 and the upper surface 1208 also cooperatively define a channel 1270 that extends from the upper surface 1264 of the slot 1200 to the upper surface 1208 of the extension plate 1200. The channel 1270 defines an opening 1272 that is substantially circular in shape and defines a constant diameter along the entire length of the channel 1270. A skilled artisan will be able to determine suitable shapes for the slot and the channel based on various considerations, including the shape and size of the connecting member and the location at which the particular vertebral plate revision apparatus will be implanted. In alternative embodiments, the slot opening may be circular, rectangular, triangular, elliptical, or any other shape. In different embodiments, the channel opening may be circular, rectangular, triangular, elliptical, or any other shape. Alternatively, the slot may extend from the upper surface to the lower surface or may be partially defined by one of the upper or lower surface in alternative embodiments. Similarly, the channel may extend from the upper surface to the lower surface or may be partially defined by one of the upper or lower surface in alternative embodiments.

The vertebral plate revision apparatus 50 also includes a connecting member 1300. The connecting member 1300 has a proximal end 1302, a distal end 1304, a main body 1306 extending from the proximal end 1302 to the distal end 1306, an upper surface 1308, a lower surface 1310, a side 1312 extending from the upper surface 1308 to the lower surface 1310, and a cavity 1314 defined by the upper surface 1308.

In the illustrated embodiment, the connecting member 1300 comprises a rivet. The side 1312 includes first and second indented portions 1320, 1322 and first and second threaded portions 1330, 1332. The first indented portion 1320 is adjacent each of the first and second threaded portions 1330, 1332 and the second indented portion 1322 is also adjacent each of the first and second threaded portions 1330, 1332. The cavity 1314 is configured to mate with a driver (not illustrated in the Figures) to allow for rotational movement of the connecting member 1300, which locks the vertebral plate revision apparatus 50 in place. In use, the connecting member 1300 is disposed within the channel 1270 of the connecting plate 1200 and the channel 1172 of the extension piece 1170 of the extension plate 1100 such that the proximal end 1302 of the connecting member 1300 is disposed above the upper surface 1208 of the connecting member and the distal end 1304 is disposed below the lower surface 1174 of the extension piece 1170. As illustrated, the connecting member 1300 locks the connecting plate 1200 and the extension plate 1100 together. The connecting member 1300 has a first position, in which the extension member 1170 may be partially rotated or slide about the connecting member 1300 such that the extension plate 1100 may be slidably moved within the slot 1260. The connecting member 1300 also has a second position, in which the extension member 1170 may not be moved within the slot 1260; the extension plate 1100 and connecting plate 1200, thus, are locked in place in the second position. In other embodiments, however, the connecting member 1300 may comprise a different structure or different device. A skilled artisan will be able to determine how to configure the connecting member and whether to use a rivet based on various considerations, including the shape and size of the extension and connecting plates and the location at which the particular vertebral plate revision apparatus will be implanted. In a different embodiment, the entire side of the connecting member may be threaded. In another embodiment, the connecting member may only have one position; such a position may either allow for sliding movement of the extension plate relative to the connecting plate or may not allow for movement of the extension plate relative to the connecting plate. Furthermore, any portion of the connecting member may be disposed within the slot, including the entirety of the connecting member. The connecting member also may be rotated by any driver or any other device in all embodiments. In other embodiments, the connecting member may also comprise a screw, a rod, a nut, a threaded boss, any type of mechanical attachment mechanism, or a mechanical attachment mechanism coated in an adhesive.

Figure 19:
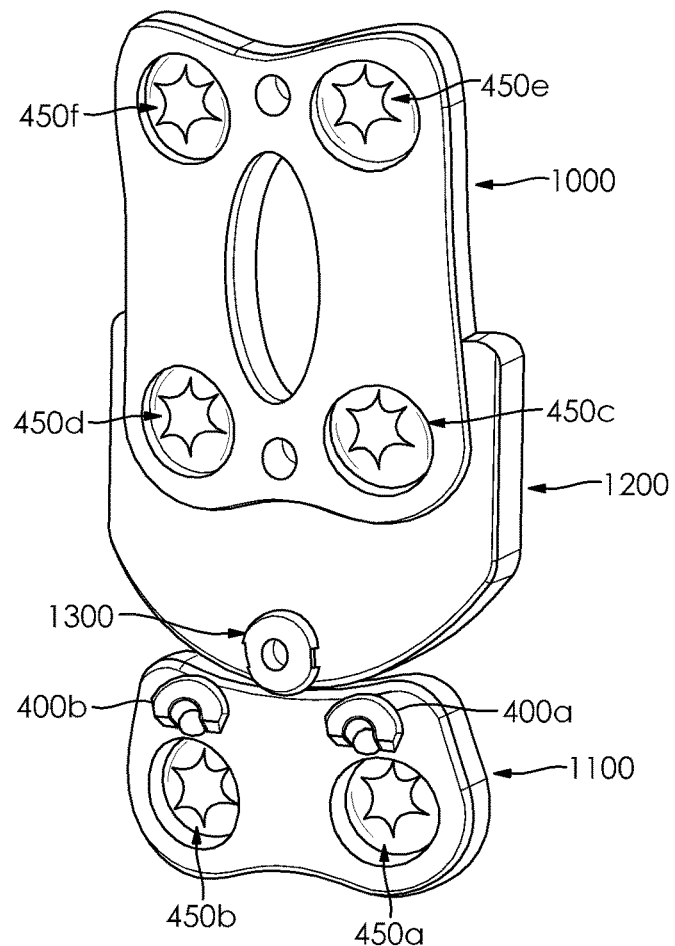
FIG. 19 is a perspective view of another osteosynthesis system.
Figure 20:
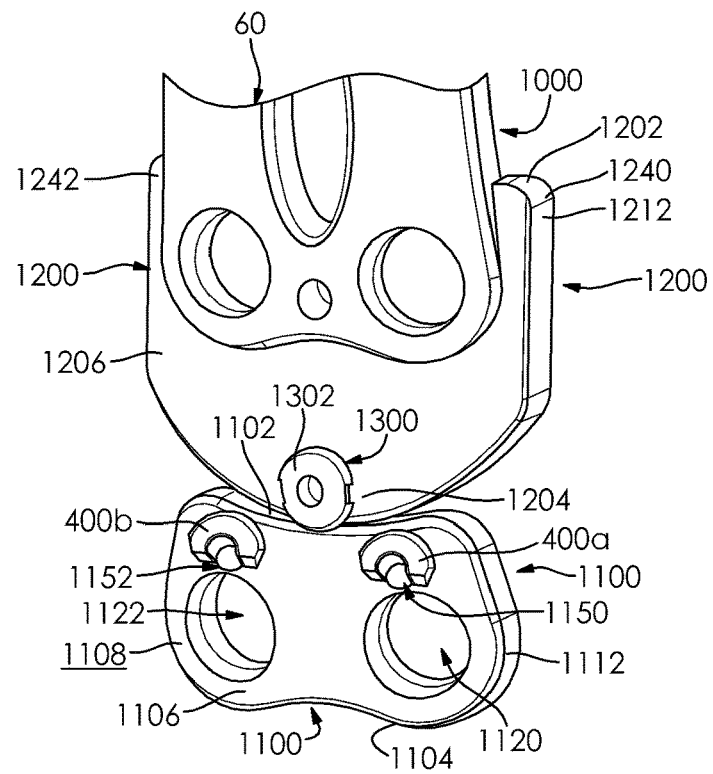
FIG. 20 is a partial perspective view of the osteosynthesis system illustrated in FIG. 19 without the anchors illustrated in FIG. 19.

Each of FIGS. 19 and 20 illustrates an osteosynthesis system 60 or a component or components thereof. FIG. 19 illustrates an extension plate 1100, a connecting plate 1200, a connecting member 1300, a previously-implanted plate 1000, a set of anchors 450a, 450b, 450c, 450d, 450e, 450f, and a set of locking members 400a, 400b.

Figure 21:
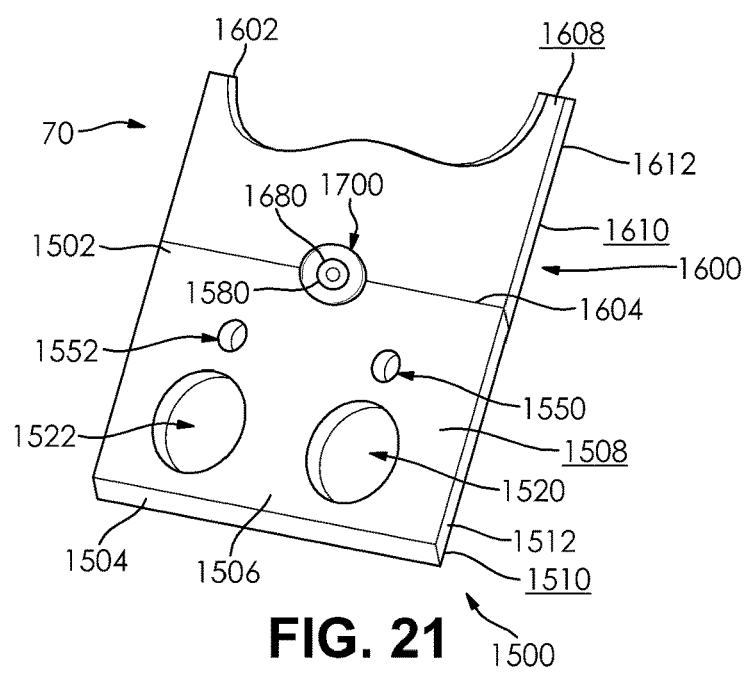
FIG. 21 is a perspective view of another example vertebral plate revision apparatus.

FIG. 21 illustrates another example vertebral plate revision apparatus 70. This example vertebral plate revision apparatus 70 includes an extension plate 1500, a connecting plate 1600, and a connecting member 1700.

The extension plate 1500 comprises a proximal end 1502, a distal end 1504, a main body 1506 extending from the proximal end 1502 to the distal end 1504, an upper surface 1508, a lower surface 1510, a side 1512 extending from the upper surface 1508 to the lower surface 1510, a set of anchor passageways 1520, 1522, a set of locking member passageways 1550, 1552, and a notch 1580 disposed on the proximal end 1502 cooperatively defined by the upper surface 1508 and the lower surface 1510.

The connecting plate 1600 comprises a proximal end 1602, a distal end 1604, a main body 1606 extending from the proximal end 1602 to the distal end 1604, an upper surface 1608, a lower surface 1610, a side 1612 extending from the upper surface 1608 to the lower surface 1610, and a notch 1680 disposed on the distal end 1604 cooperatively defined by the upper surface 1608 and the lower surface 1610.

The vertebral plate revision apparatus 70 also includes a connecting member 1700.

Figure 22:
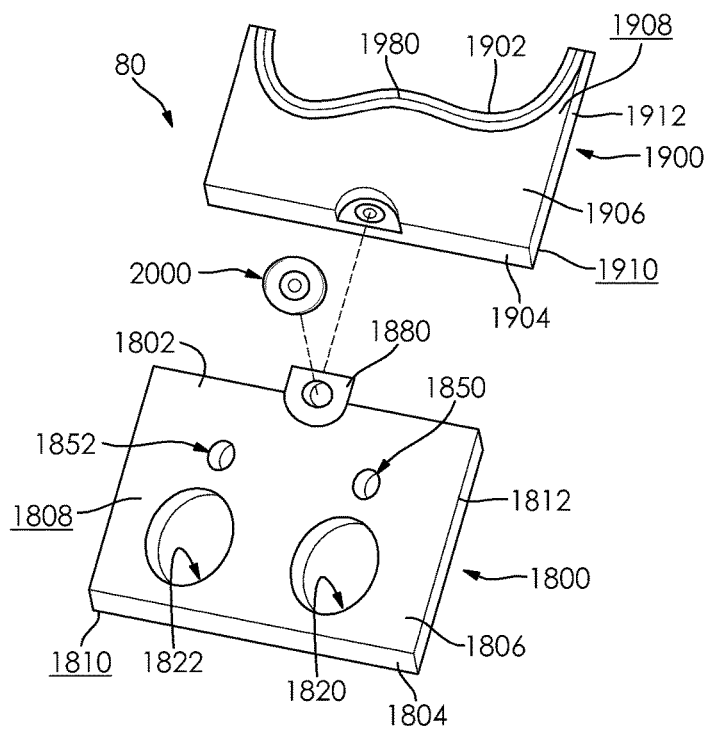
FIG. 22 is an exploded view of another example vertebral plate revision apparatus.

FIG. 22 illustrates another example vertebral plate revision apparatus 80. This example vertebral plate revision apparatus 80 includes an extension plate 1800, a connecting plate 1900, and a connecting member 2000.

The extension plate 1800 comprises a proximal end 1802, a distal end 1804, a main body 1806 extending from the proximal end 1802 to the distal end 1804, an upper surface 1808, a lower surface 1810, a side 1812 extending from the upper surface 1808 to the lower surface 1810, a set of anchor passageways 1820, 1822, a set of locking member passageways 1850, 1852, and an extension piece 1880.

The connecting plate 1900 comprises a proximal end 1902, a distal end 1904, a main body 1906 extending from the proximal end 1902 to the distal end 1904, an upper surface 1908, a lower surface 1910, a side 1912 extending from the upper surface 1908 to the lower surface 1910, a slot 1960, and a lip 1980 defined by the side 1912.

The vertebral plate revision apparatus 80 also includes a connecting member 2000.

Figure 23:
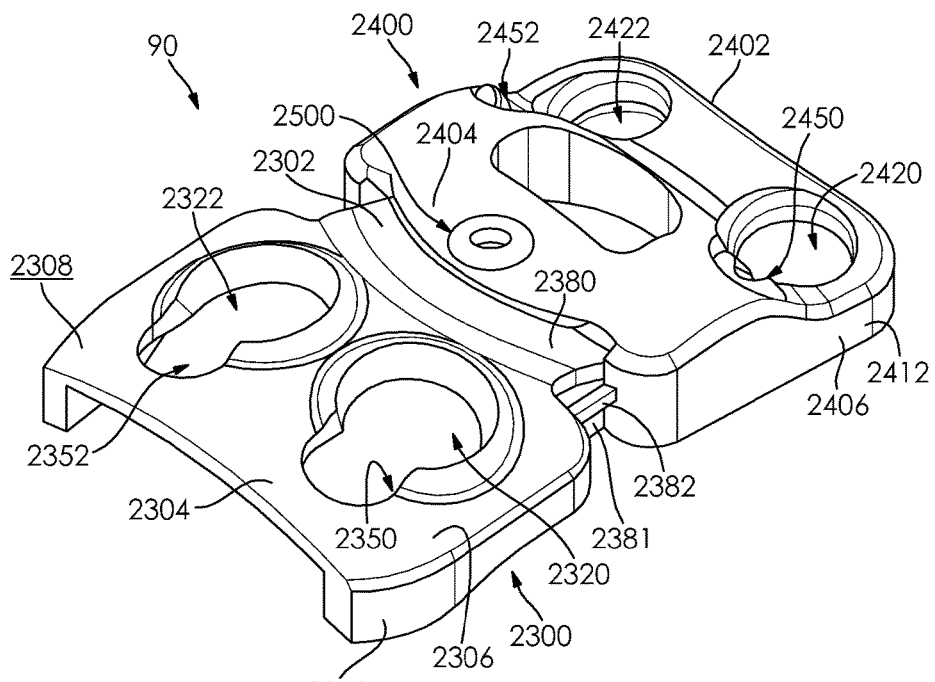
FIG. 23 is a perspective view of another example vertebral plate revision apparatus.
Figure 24:
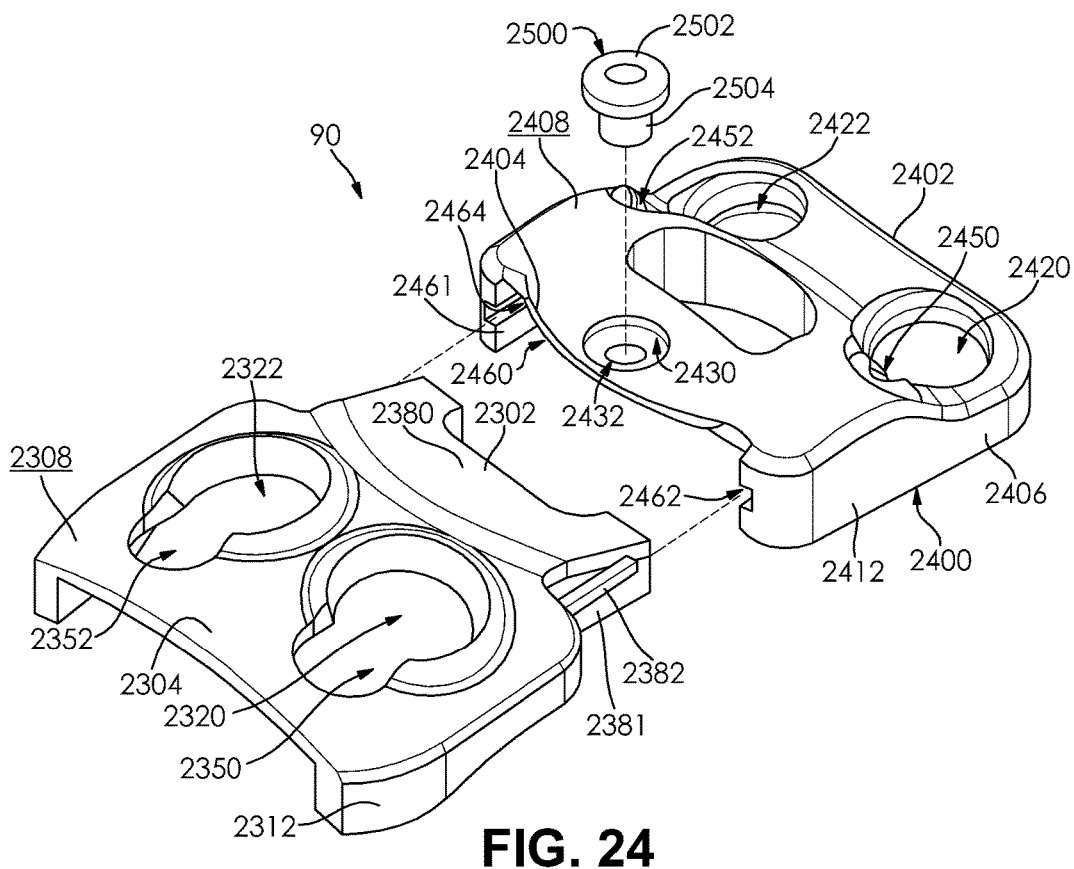
FIG. 24 is an exploded view of another example vertebral plate revision apparatus.

FIGS. 23 and 24 illustrate another example vertebral plate revision apparatus 90. This example vertebral plate revision apparatus 90 includes an extension plate 2300, a connecting plate 2400, and a connecting member 2500.

The extension plate 2300 comprises a proximal end 2302, a distal end 2304, a main body 2306 extending from the proximal end 2302 to the distal end 2304, an upper surface 2308, a lower surface (not illustrated in the Figures), a side 2312 extending from the upper surface 2308 to the lower surface, a set of anchor passageways 2320, 2322, a set of locking member passageways 2350, 2352, and an extension piece 2380.

The connecting plate 2400 comprises a proximal end 2402, a distal end 2404, a main body 2406 extending from the proximal end 2402 to the distal end 2404, an upper surface 2408, a lower surface (not illustrated in the Figures), a side 2412 extending from the upper surface 2408 to the lower surface, a set of anchor passageways 2420, 2422, a set of locking member passageways 2450, 2452, and a slot 2460.

The vertebral plate revision apparatus 90 also includes a connecting member 2500 having a proximal end 2502 and a distal end 2504.

The extension piece 2380 is defined by the proximal end 2302 of the extension plate 2300 and extends away from the distal end 2304. The extension piece 2380 is configured to be engaged by a slot defined by the connecting plact 2400 (described below). Accordingly, the extension piece defines a first railing 2382 disposed on the side 2381 of the extension piece 2380 and a second railing (not illustrated in the Figures) disposed on the side 2381 of the extension piece 2380. A skilled artisan will be able to suitably configure an extension piece according to a particular example based on various considerations, including the size and shape of the connecting plate and the connecting member. In a different embodiment, any other mechanical attachment can be used in place of one or both of the first and second railings. In various other embodiments, zero, one, three, or more than three railings may be used in place of one or both of the first and second railings.

The extension piece 2380 also defines a channel (not illustrated in the Figures) configured to engage a portion of the connecting member.

The connecting plate 2400 defines a slot 2460 disposed on its distal end 2404 that is configured to allow for the extension piece 2380 of the extension plate 2300 to slidably engage first and second interior slots 2462, 2464 defined by an interior wall 2461 of the connecting plate 2460. More specifically, the first interior slot 2462 is configured to allow the first railing 2382 to be slidably disposed within the connecting piece 2400 and the second interior slot 2464 is configured to allow the second railing to be slidably disposed within the connecting piece 2400. This allows for a user of the device to insert the extension piece 2380 within the slot 2460 and manipulate the extension plate 2300 relative to the connecting plate 2400. However, in other embodiments the connecting plate may not define a slot. A skilled artisan will be able to suitably determine how to engage the connecting and extension plates according to a particular example based on various considerations, including the size and shape of the connecting member and the particular anatomy in which the device will be placed. In a different embodiment, any other mechanical attachment may be used in place of one or more of first and second interior slots and/or slot. In various other embodiments, zero, one, three, or more than three interior slots may be used.

The connecting plate 2400 also defines a recess 2430 in fluid communication with a channel 2432. The recess 2430 and channel 2432 are configured such that the connecting member 2500 may be disposed within the recess 2430 and channel 2432 in order to engage the connecting plate 2400 and the extension plate 2300. More specifically, the proximal end 2502 is substantially disposed within the recess 2430 and the distal end 2504 is substantially disposed within the channel 2432 of the connecting plate 2400 and the channel of the extension piece 2380 when the vertebral plate revision apparatus 90 is in use.

Figure 25:
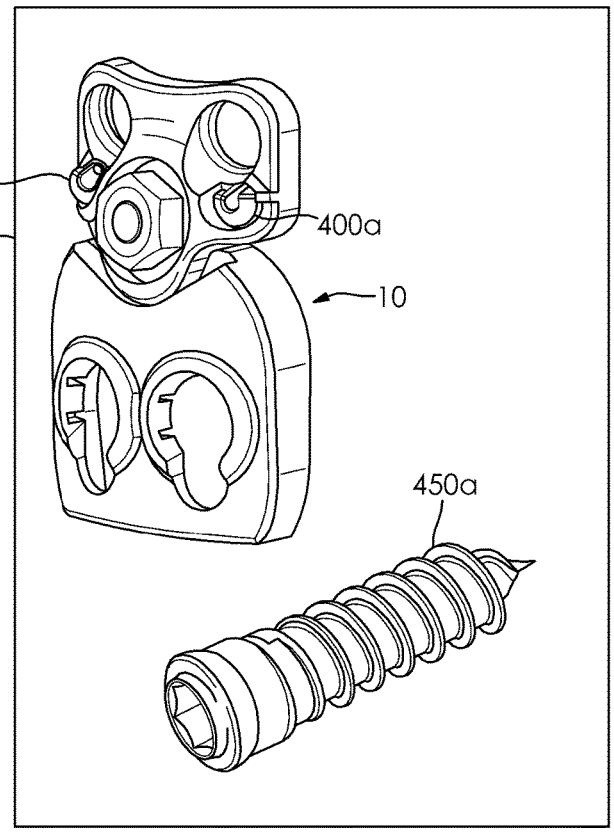
FIG. 25 is a schematic illustration of an example kit.

FIG. 25 illustrates an example kit 2100 comprising a vertebral plate revision apparatus according to an example embodiment, such as vertebral plate revision apparatus 10 illustrated, for example, in FIG. 1; a set of locking members according to an embodiment, such as locking members 400a, 400b illustrated, for example, in FIG. 1; and at least one anchor according to an embodiment, such as anchor 450a illustrated, for example, in FIG. 9. In other embodiments, any anchor plate revision apparatus may be used, including one of anchor plate revision apparatuses 20, 30, 50, 70, 80.

While a single vertebral plate revision apparatus 10 is illustrated in FIG. 25, a plurality of vertebral plate revision apparatuses may be included in the kit 2100, as well. In addition more than or fewer than two locking members may be included in the kit; these locking members may have different sizes and shapes. Multiple anchors may also be included in the kit and each anchor may be sized and shaped differently than any other anchor. In addition, other tools or devices, such as another plate or a driver, may also be included in the kit. A skilled artisan will be able to select a suitable number of vertebral plate revision apparatuses, locking members, and anchors for inclusion in a kit based on various considerations, including the location at which the particular vertebral plate revision apparatus will be implanted.

Figure 26:
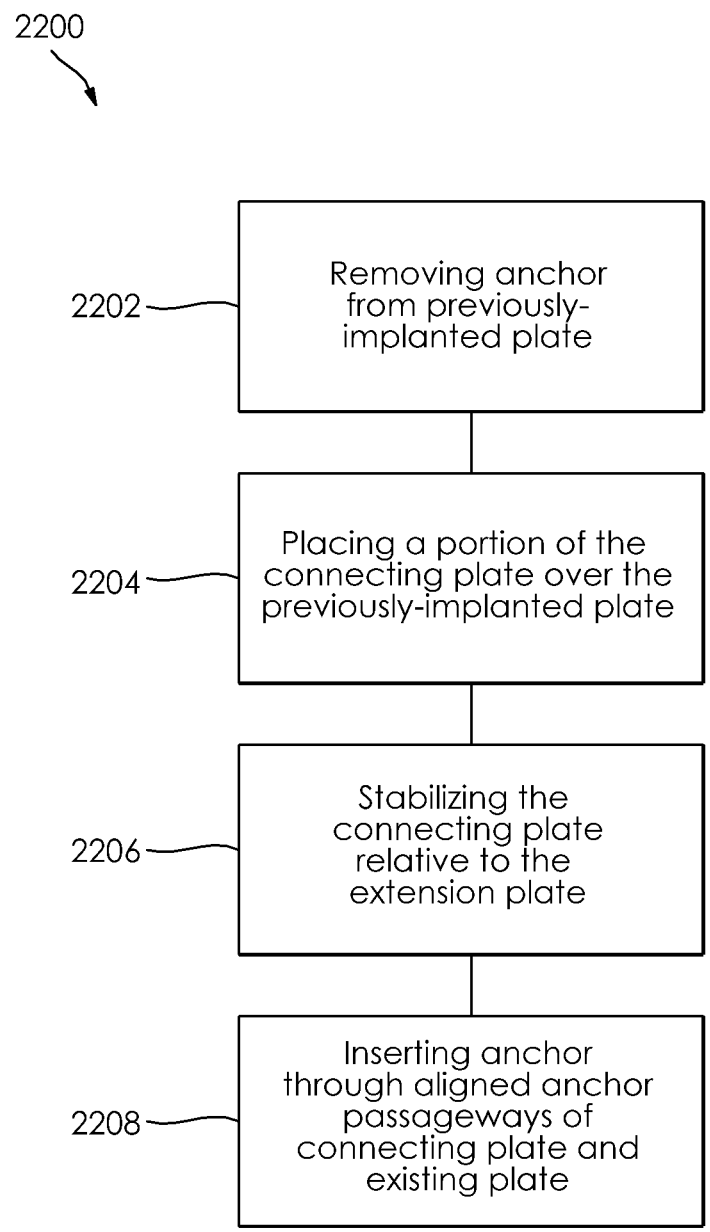
FIG. 26 is a flowchart representation of an example method of engaging a vertebral plate revision apparatus with a previously-implanted plate.

FIG. 26 is a flowchart representation of an example method 2200 of engaging a vertebral plate revision apparatus with a previously-implanted plate. Performance of this method results in the engagement of the vertebral plate revision apparatus with the previously-implanted plate and to a bone or a portion of a bone. This method can be used for engaging any type of vertebral plate revision apparatus with any type of previously-implanted plate. The method can also be used for engaging any type of vertebral plate revision apparatus with a plate that has not yet been implanted in a body. In this method, engaging a vertebral plate revision apparatus with a previously-implanted plate comprises engagement of the connecting plate with the previously-implanted plate. In other methods, the entire connecting plate may be placed over the previously-implanted plate or a portion of the extension plate may be placed over the previously-implanted plate.

An initial step 2202 comprises removing an anchor or more than one anchors from a previously-implanted plate. Previously-implanted plate 1000 and anchors 450c, 450d, 450e, 450f are described in this step 2202. More specifically, anchors 450c, 450d are removed from the anchor passageways 1020, 1022, respectively, of previously-implanted plate 1000. In other embodiments, anchors 450e, 450f may be removed from anchor passageways. In different embodiments, only one anchor or more than two anchors may be removed from the anchor passageways. Additionally, the previously-implanted plate may comprise any plate and the anchors may comprise any anchors.

Another step 2204 comprises placing a portion of the connecting plate of a vertebral plate revision apparatus over the previously-implanted plate 1000. Vertebral plate revision apparatus 10 is described in this step. The connecting plate 200 of the vertebral plate revision apparatus 10 is placed over the previously-implanted plate 1000 such that the anchor passageways 220, 222 of the connecting plate 200 are aligned with the anchor passageways 1020, 1022 of the previously-implanted plate. No movement of the vertebral plate revision apparatus 10 along the vertebral column is necessary; the engaging recess 260 of the connecting plate 200 is configured such that it may engage the previously-implanted plate 1000 without moving proximally, distally, or horizontally with respect to the vertebral column and previously-implanted plate 1000. The vertebral plate revision apparatus may also comprise any of the aforementioned vertebral plate apparatuses 20, 30, 50, 70, 80. In other embodiments, the connecting plate may be partially or fully placed under the previously-implanted plate.

Another step 2206 comprises stabilizing the connecting plate 200 of relative to the extension plate 100. The connecting plate 200 is stabilized relative to the extension plate 100 via the tightening of the connecting member 300 in this method. The connecting member 300 is tightened, producing compressive force between the extension and connecting plates 100, 200, after the connecting plate 200 and extension plate 100 have been suitably aligned with one another. More specifically, the connecting member 300 is tightened after the proximal end 102 of the extension plate 100 have been suitably aligned with the distal end 204 of the connecting plate 200, as described above. The connecting member 300 may be manually tightened or may be tightened by a driver, a screwdriver, a wrench, or any other similar device. In other methods, the stabilizing step may include the use of rotational force, an adhesive, or any other stabilizing force.

Another step 2208 comprises inserting one or more of anchors 450a, 450b, 450c, 450d through one or more of anchor passageways 120, 122, 220, 222 of the vertebral plate revision apparatus 10 and, in some instances, one or more of anchor passageways 1020, 1022 of the previously-implanted plate 1000, such that the connecting plate 200 is secured to the previously-implanted plate 1000. More specifically, anchor 450a is disposed through anchor passageway 120 of the extension plate 100 such that it is in contact with a bone or a portion of a bone. Anchor 450b is disposed through anchor passageway 122 of the extension plate 100 such that it is in contact with a bone or a portion of a bone. Anchor 450c is disposed through aligned anchor passageway 220 of the connecting plate 200 and anchor passageway 1020 of the previously-implanted plate 1000 such that it is in contact with a bone or a portion of a bone. Anchor 450d is disposed through aligned anchor passageway 222 of the connecting plate 200 and anchor passageway 1022 of the previously-implanted plate 1000 such that it is in contact with a bone or a portion of a bone. In other embodiments, few than or more than four anchors may be inserted through the aforementioned anchor passageways. Additionally, more than one anchor may be inserted through a particular anchor passageway in different embodiments. Alternatively, one or more anchor may not contact a bone in other embodiments.

It is noted that the method 2200 may be completed in the order illustrated and described. However, the steps may also be completed in any order.

The vertebral plate revision apparatuses, kits, and methods and osteosynthesis systems are useful in a variety of orthopedic procedures. Particular embodiments, including the specific embodiments illustrated and described in detail herein, are useful in a variety of cervical related orthopedic procedures, including Anterior Cervical Surgery (ACS) and Anterior Cervical Discectomy and Fusion (ACDF) procedures. An ACS procedure can involve augmentation of the vertebral body and/or uncinate process from an anterior approach. An ACDF procedure can involve performing a decompression of the nerve roots through a discectomy anteriorly and performing an interbody fusion to avoid radiculopathy from foraminal narrowing and the possibility of developing late kyphosis from disc space collapse.

All components of the vertebral plate revision apparatuses, kits, and methods, and osteosynthesis systems can be made from any suitable material. Non-limiting examples of suitable materials include metals, such as stainless steel, titanium, cobalt-chromium, and other metals, plastics commonly used in medical devices, Nitinol and other superelastic materials, polyurethane materials, silicone materials, and polyether ether ketone (PEEK) materials.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

We claim:

1. A vertebral plate revision apparatus configured to engage a previously-implanted plate, comprising:
   an extension plate having an extension plate upper surface, an extension plate lower surface, an extension plate side extending from the extension plate upper surface to the extension plate lower surface, and an extension plate main body defining a set of extension plate anchor passageways extending from the extension plate upper surface to the extension plate lower surface, a set of extension plate locking member passageways, an extension plate connecting member recess, a connecting member passageway, and a first base, the extension plate connecting member recess extending from the extension plate upper surface toward the extension plate lower surface to the first base, the connecting member passageway extending from the first base;
   a connecting plate having a connecting plate proximal end, a connecting plate distal end, a connecting plate upper surface, a connecting plate lower surface, a connecting plate side extending from the connecting plate upper surface to the connecting plate lower surface, and a connecting plate main body defining a set of connecting plate anchor passageways, a set of connecting plate locking member passageways, a connecting plate connecting member recess, a second base, and a boss disposed on the second base and through the connecting member passageway; and
   a connecting member having a connecting member upper surface, a connecting member lower surface, a connecting member side extending from the connecting member upper surface to the connecting member lower surface, and a connecting member channel extending from the connecting member upper surface to the connecting member lower surface, the connecting member releasably attached to the boss and adjacent the first base;
   wherein the extension plate is pivotally adjustable about the boss relative to the connecting plate.

2. The vertebral plate revision apparatus of claim 1, wherein the extension plate has an extension plate first portion and an extension plate second portion, the first portion defining the set of extension plate anchor passageways and the set of extension plate locking member passageways; and
   wherein the second portion of the extension plate is in contact with the second base.

3. The vertebral plate revision apparatus of claim 2, wherein the connecting member passageway has a connecting member passageway upper opening and a connecting member passageway lower opening;
   wherein the first base defines the connecting member passageway upper opening; and
   wherein the second portion defines the connecting member passageway lower opening.

4. The vertebral plate revision apparatus of claim 1, wherein the connecting plate main body defines an engaging recess and an engaging recess base:
   wherein the engaging recess extends from the connecting plate proximal end and the connecting plate lower surface; and
   wherein each connecting plate anchor passageway extends from the connecting plate upper surface to the engaging recess base.

5. The vertebral plate revision apparatus of claim 4, wherein each connecting plate locking member passageway extends from the connecting plate upper surface to the engaging recess base.

6. The vertebral plate revision apparatus of claim 4, wherein the connecting plate main body defines a first flange, a second flange, a third flange, and a fourth flange, each of the first flange, the second flange, the third flange, and the fourth flange configured to engage said previously-implanted plate.

7. The vertebral plate revision apparatus of claim 6, wherein the first flange and the second flange are disposed adjacent a first connecting plate anchor passageway of the set of connecting plate anchor passageways; and
wherein the third flange and the fourth flange are disposed adjacent a second connecting plate anchor passageway of the set of connecting plate anchor passageways.

8. The vertebral plate revision apparatus of claim 1, wherein a first extension plate anchor passageway of the set of extension plate anchor passageways has a first diameter;
wherein a second extension plate anchor passageway of the set of extension plate anchor passageways has a second diameter that is equal to the first diameter;
wherein a first extension plate locking member passageway of the set of extension plate locking member passageways has a third diameter;
wherein a second extension plate locking member passageway of the set of extension plate locking member passageways has a fourth diameter that is equal to the third diameter; and
wherein each of the third diameter and fourth diameter is less than each of the first diameter and the second diameter.

9. The vertebral plate revision apparatus of claim 1, wherein the boss has an outer surface that defines threads.

10. The vertebral plate revision apparatus of claim 9, wherein the connecting member has a connecting member main body defining an inner surface that defines threads within the connecting member channel; and
wherein the threads of the boss are configured to mate with the threads of the connecting member.

11. The vertebral plate revision apparatus of claim 1, wherein each extension plate locking member passageway is in communication with an extension plate anchor passageway of the set of extension plate anchor passageways.

12. The vertebral plate revision apparatus of claim 1, wherein each connecting plate locking member passageway is in communication with a connecting plate anchor passageway of the set of connecting plate anchor passageways.

13. A vertebral plate revision apparatus configured to engage a previously-implanted plate, comprising:
an extension plate having an extension plate upper surface, an extension plate lower surface, an extension plate side extending from the extension plate upper surface to the extension plate lower surface, and an extension plate main body defining a set of extension plate anchor passageways extending from the extension plate upper surface to the extension plate lower surface, a set of extension plate locking member passageways, an extension plate connecting member recess, an extension plate first portion, an extension plate second portion, a connecting member passageway, and a first base, the extension plate connecting member recess extending from the extension plate upper surface toward the extension plate lower surface to the first base, the first portion defining the set of extension plate anchor passageways and the set of extension plate locking member passageways, the connecting member passageway having a connecting member passageway upper opening defined by the first base and a connecting member passageway lower opening defined by the second portion;
a connecting plate having a connecting plate proximal end, a connecting plate distal end, a connecting plate upper surface, a connecting plate lower surface, a connecting plate side extending from the connecting plate upper surface to the connecting plate lower surface, and a connecting plate main body defining a set of connecting plate anchor passageways, a set of connecting plate locking member passageways, a connecting plate connecting member recess, a second base, a boss disposed on the second base and through the connecting member passageway, an engaging recess, and an engaging recess base, the engaging recess extending from the connecting plate proximal end and the connecting plate lower surface, each connecting plate anchor passageway extending from the connecting plate upper surface to the engaging recess base; and
a connecting member having a connecting member upper surface, a connecting member lower surface, a connecting member side extending from the connecting member upper surface to the connecting member lower surface, and a connecting member channel extending from the connecting member upper surface to the connecting member lower surface, the connecting member releasably attached to the boss and adjacent the first base;
wherein the extension plate is pivotally adjustable about the boss relative to the connecting plate; and
wherein the second portion of the extension plate is in contact with the second base.

14. The vertebral plate revision apparatus of claim 13, wherein each connecting plate locking member passageway extends from the connecting plate upper surface to the engaging recess base.

15. The vertebral plate revision apparatus of claim 13, wherein the connecting plate main body defines a first flange, a second flange, a third flange, and a fourth flange, each of the first flange, the second flange, the third flange, and the fourth flange configured to engage said previously-implanted plate.

16. The vertebral plate revision apparatus of claim 15, wherein the first flange and the second flange are disposed adjacent a first connecting plate anchor passageway of the set of connecting plate anchor passageways; and
wherein the third flange and the fourth flange are disposed adjacent a second connecting plate anchor passageway of the set of connecting plate anchor passageways.

17. The vertebral plate revision apparatus of claim 13, wherein a first extension plate anchor passageway of the set of extension plate anchor passageways has a first diameter;
wherein a second extension plate anchor passageway of the set of extension plate anchor passageways has a second diameter that is equal to the first diameter;
wherein a first extension plate locking member passageway of the set of extension plate locking member passageways has a third diameter;
wherein a second extension plate locking member passageway of the set of extension plate locking member passageways has a fourth diameter that is equal to the third diameter; and
wherein each of the third diameter and fourth diameter is less than each of the first diameter and the second diameter.

18. The vertebral plate revision apparatus of claim 13, wherein the boss has an outer surface that defines threads.

19. The vertebral plate revision apparatus of claim 18, wherein the connecting member has a connecting member main body defining an inner surface that defines threads within the connecting member channel; and
wherein the threads of the boss are configured to mate with the threads of the connecting member.

20. A vertebral plate revision apparatus configured to engage a previously-implanted plate, comprising:

an extension plate having an extension plate upper surface, an extension plate lower surface, an extension plate side extending from the extension plate upper surface to the extension plate lower surface, and an extension plate main body defining a set of extension plate anchor passageways extending from the extension plate upper surface to the extension plate lower surface, a set of extension plate locking member passageways, an extension plate first portion, an extension plate second portion, a connecting member passageway, an extension plate connecting member recess, and a first base, each extension plate locking member passageway in communication with an extension plate anchor passageway of the set of extension plate anchor passageways, the extension plate connecting member recess extending from the extension plate upper surface toward the extension plate lower surface to the first base, the first portion defining the set of extension plate anchor passageways and the set of extension plate locking member passageways, the connecting member passageway having a connecting member passageway upper opening defined by the first base and a connecting member passageway lower opening defined by the second portion;

a connecting plate having a connecting plate proximal end, a connecting plate distal end, a connecting plate upper surface, a connecting plate lower surface, a connecting plate side extending from the connecting plate upper surface to the connecting plate lower surface, and a connecting plate main body defining a set of connecting plate anchor passageways, a set of connecting plate locking member passageways, a connecting plate connecting member recess, a second base, an engaging recess, an engaging recess base, and a boss, each connecting plate locking member passageway in communication with a connecting plate anchor passageway of the set of connecting plate anchor passageways, the engaging recess extending from the connecting plate proximal end and the connecting plate lower surface, the boss disposed on the second base and through the connecting member passageway, the boss having an outer surface that defines threads, each connecting plate anchor passageway extending from the connecting plate upper surface to the engaging recess base, each connecting plate locking member passageway extending from the connecting plate upper surface to the engaging recess base; and a connecting member having a connecting member upper surface, a connecting member lower surface, a connecting member side extending from the connecting member upper surface to the connecting member lower surface, and a connecting member main body defining a connecting member channel and an inner surface, the connecting member channel extending from the connecting member upper surface to the connecting member lower surface, the inner surface defining threads within the connecting member channel that are configured to mate with the threads of the boss, the connecting member releasably attached to the boss and adjacent the first base;

wherein the extension plate is pivotally adjustable about the boss relative to the connecting plate; and wherein the second portion of the extension plate is in contact with the second base.

* * * * *